(12) United States Patent
Riley et al.

(10) Patent No.: US 9,228,172 B2
(45) Date of Patent: Jan. 5, 2016

(54) INDUCIBLE REGULATORY T-CELL GENERATION FOR HEMATOPOIETIC TRANSPLANTS

(75) Inventors: James L. Riley, Downingtown, PA (US); Carl H. June, Merion Station, PA (US); Bruce R. Blazar, Golden Valley, MN (US); Keli Hippen, Robbinsdale, MN (US)

(73) Assignees: The Trustees of the University of Pennsylvania, Philadelphia, PA (US); Regents of the University of Minnesota, Minneapolis, MN (US)

( * ) Notice: Subject to any disclaimer, the term of this patent is extended or adjusted under 35 U.S.C. 154(b) by 471 days.

(21) Appl. No.: 12/999,926

(22) PCT Filed: Jun. 19, 2009

(86) PCT No.: PCT/US2009/047887
§ 371 (c)(1),
(2), (4) Date: May 13, 2011

(87) PCT Pub. No.: WO2009/155477
PCT Pub. Date: Dec. 23, 2009

(65) Prior Publication Data
US 2011/0268752 A1    Nov. 3, 2011

Related U.S. Application Data

(60) Provisional application No. 61/132,601, filed on Jun. 19, 2008.

(51) Int. Cl.
| C12N 5/071 | (2010.01) |
| C12N 5/00 | (2006.01) |
| C12N 5/02 | (2006.01) |
| C12N 5/0783 | (2010.01) |
| A61K 39/00 | (2006.01) |
| A61K 35/12 | (2015.01) |

(52) U.S. Cl.
CPC ............ *C12N 5/0636* (2013.01); *A61K 39/001* (2013.01); *A61K 2035/122* (2013.01); *A61K 2039/5158* (2013.01); *C12N 2501/065* (2013.01); *C12N 2501/70* (2013.01); *C12N 2501/999* (2013.01)

(58) Field of Classification Search
None
See application file for complete search history.

(56) References Cited

U.S. PATENT DOCUMENTS

| 2006/0034810 A1 | 2/2006 | Riley et al. | |
| 2006/0115899 A1* | 6/2006 | Buckner et al. | 435/372 |
| 2006/0286067 A1* | 12/2006 | Horwitz et al. | 424/85.1 |
| 2009/0257988 A1* | 10/2009 | Horwitz et al. | 424/93.7 |

FOREIGN PATENT DOCUMENTS

WO    WO2007/037544    4/2007

OTHER PUBLICATIONS

Current Protocols in Immunology, 2004, pp. 3.12.1-3.12.20.*
Fallarino et al., 2006, J. Immunol. vol. 176: 6752-6761.*
Kim et al., 2007, J. Exp. Med. vol. 204: 1543-1551.*
Singal et al., 1999, Blood. vol. 93: 4059-70.*
Kopf et al., pblished online Sep. 2007, Int. Immunopharmacol. vol. 7: 1819-24.*
Golovina et al., 2008, J. Immunol. vol. 181: 2855-68.*
Delgoffe et al., 2009, Immunology, vol. 127: 459-65.*
Ito et al., PNAS, 2006, vol. 103: 13138-43.*
Curti et al., 2007, Blood. vol. 109: 2871-77.*
Long et al., published online Mar. 2008, J. Autoimmunity, pp. 1-10.*
Baron et al., "DNA demethylation in the human FOXP3 locus discriminates regulatory T cells from activated FOXP3+ convention cells." 2007 Eur J. Immunol 27:2378-2389.
Battaglia et al., "Rapamycin selectively expands CD4+CD25+FoxP3+ regulatory T cells." 2005, Blood 105:4743-4748.
Coenen et al., "Rapamycin, and not cyclosporin A, preserves the highly suppressive CD27+ subset of human CD4+CD25+ regulatory T cells." 2006, Blood 107:1018-1023.
Daskalakis et al., "Demethylation of hypemethylated P15/INK4B gene in patients with myelodysplastic syndrome by 5-aza-2'-deoxycytidine (decitibine) treatment." 2002 Blood 100:2957-2964.
DiPaulo et al. "Autoantigen-specific TGFbeta-induded FoxP3+ regulatory T cells prevent autoimmunity by inhibiting dendritic cells from activating autoreactive T cells" 2007 Journal of Immunology 179:4585-4693.
Dokmanovic et al., "Histone deacetylase inhibitors selectively suppress expression of HDAC7.", 2007 Mol. Cancer Ther 6:2525-2534.
Floess et al., "Epigenetic control of the foxp3 locus in regulatory T cells." 2007, PLoS Biol 5:e38.
Haxhinasto et al., "The AKT-mTOR axis regulates de novo differentiation of CD4+Foxp3+ cells." 2008, J Exp Med 205(3):565-574.
Sharma et al., "Plasmacytoid dendritic cells from mouse tumor-draining lymph nodes directly activate mature Tregs via indoleamine 2,3-dioxygenase." 2007 J Clin Invest 117:2570-2582 (abstract).
Tao et al., "Deacetylase inhibition promotes the generation and function of regulatory T cells." 2007, Nat Med 13:1299-1307.
Zeiser et al., "Differential impact of mammalian target of rapamycin inhibition on CD4+CD25+Foxp3+ regulatory T cells compared with conventional CD4+ T cells." 2008, Blood 111:453-462.

\* cited by examiner

*Primary Examiner* — Amy Juedes
(74) *Attorney, Agent, or Firm* — Saul Ewing LLP; Kathryn Doyle; Kelly J. Morgan

(57) ABSTRACT

The present invention provides methods and compositions for converting non-Tregs into Tregs. The converted Tregs are referred to as inducible Tregs (iTregs). The iTregs are useful for preventing, suppressing, blocking or inhibiting an immune response. For example the iTregs are useful for preventing rejection of a transplanted tissue in a human or other animal host, or protecting against graft vs host disease. The iTregs can also be used to treat autoimmune diseases.

13 Claims, 14 Drawing Sheets

INDUCIBLE REGULATORY T-CELL GENERATION FOR HEMATOPOIETIC TRANSPLANTS

CROSS-REFERENCE TO RELATED APPLICATIONS

The present application is the U.S. national phase application filed under 35 U.S.C. §371 claiming benefit to International Patent Application No. PCT/US 09/47887, filed on Jun. 19, 2009, which is entitled to priority under 35U.S.C. §119 (e) to U.S. Provisional Patent Application No. 61/132,601, filed on Jun. 19, 2008, each of which application is hereby incorporated herein by reference in its entirety

BACKGROUND OF THE INVENTION

The mammalian immune system plays a central role in protecting individuals from infectious agents and preventing tumor growth. However, the same immune system can produce undesirable effects such as the rejection of cell, tissue and organ transplants from unrelated donors. The immune system does not distinguish beneficial intruders, such as a transplanted tissue, from those that are harmful, and thus the immune system rejects transplanted tissues or organs. Rejection of transplanted organs is generally mediated by alloreactive T cells present in the host which recognize donor alloantigens or xenoantigens.

The transplantation of cells, tissues, and organs between genetically disparate individuals invariably results in the risk of graft rejection. Nearly all cells express products of the major histocompatibility complex, MHC class I molecules. Further, many cell types can be induced to express MHC class II molecules when exposed to inflammatory cytokines. Additional immunogenic molecules include those derived from minor histocompatibility antigens such as Y chromosome antigens recognized by female recipients. Rejection of allografts is mediated primarily by T cells of both the CD4 and CD8 subclasses (Rosenberg et al., 1992, Annu. Rev. Immunol. 10:333). Alloreactive CD4+ T cells produce cytokines that exacerbate the cytolytic CD8 response to alloantigen. Within these subclasses, competing subpopulations of cells develop after antigen stimulation that are characterized by the cytokines they produce. Th1 cells, which produce IL-2 and IFN-γ, are primarily involved in allograft rejection (Mossmann et al., 1989, Annu. Rev. Immunol. 7:145). Th2 cells, which produce IL-4 and IL-10, can down-regulate Th1 responses through IL-10 (Fiorentino et., 1989, J. Exp. Med. 170:2081). Indeed, much effort has been expended to divert undesirable Th1 responses toward the Th2 pathway. Undesirable alloreactive T cell responses in patients (allograft rejection, graft-versus-host disease) are typically handled with immunosuppressive drugs such as prednisone, azathioprine, and cyclosporine A. Unfortunately, these drugs generally need to be maintained for the life of the patient and they have a multitude of dangerous side effects including generalized immunosuppression.

Peripheral blood contains a small population of T cell lymphocytes that express the T regulatory phenotype ("Treg"), i.e., positive for both CD4 and CD25 antigens. There are several subsets of Treg cells (Bluestone et al., 2003 Nature Rev. Immunol. 3: 253). One subset of regulatory cells develops in the thymus. Thymic derived Treg cells function by a cytokine-independent mechanism, which involves cell to cell contact (Shevach, 2002 Nature Rev. Immunol 2: 389). They are essential for the induction and maintenance of self-tolerance and for the prevention of autoimmunity (Shevach, 2000 Annu. Rev. Immunol. 18: 423-449). These regulatory cells prevent the activation and proliferation of autoreactive T cells that have escaped thymic deletion or recognize extrathymic antigens, thus they are critical for homeostasis and immune regulation, as well as for protecting the host against the development of autoimmunity. Thus, immune regulatory $CD4^+CD25^+$ T cells are often referred to as "professional suppressor cells."

Naturally arising $CD4^+CD25^+$ Treg cells are a distinct cell population of cells that are positively selected on high affinity ligands in the thymus and that have been shown to play an important role in the establishment and maintenance of immunological tolerance to self antigens. Deficiencies in the development and/or function of these cells have been associated with severe autoimmunity in humans and various animal models of congenital or induced autoimmunity.

Treg cells manifest their tolerogenic effects directly via cell-to-cell contact or indirectly via soluble factors. Although the suppressive mechanisms of these cells remain to be fully elucidated, blockade of IL-2 expression in effector T cells (Teff), physical elimination of Teff cells, induction of tolerogenic dendritic cells (DCs) via CTLA-4/B7 axis, and inhibition of Teff cells via TGF-β and IL-10 are some of the mechanisms that have been implicated to date. It also has been shown that reverse signaling through CTLA-4/CD80 into Teff cells plays an important role in their inhibition by Treg cells. Similarly, interactions between CTLA-4 on Treg cells and CD80 on DCs can result in reverse signaling and upregulation of the indoleamine dioxygenase enzyme that is involved in tolerance via the regulation of tryptophan metabolism.

Treg cells can also be generated by the activation of mature, peripheral $CD4^+$ T cells. Studies have indicated that peripherally derived Treg cells mediate their inhibitory activities by producing immunosuppressive cytokines, such as transforming growth factor-beta (TGF-β) and IL-10 (Kingsley et al., 2002 J. Immunol. 168: 1080; Nakamura et al., 2001 J. Exp. Med. 194: 629-644). Treg are have been described in the literature as being hypoproliferative in vitro (Sakaguchi, 2004 Ann. Rev. Immunol, 22: 531). Trenado et al. provided the first evaluation of the therapeutic efficacy of ex vivo activated and expanded $CD4^+CD25^+$ regulatory cells in an in vivo mouse model of disease (Trenado et al., 2002 J. Clin. Invest. 112(11): 1688-1696).

However, the inadequacy of isolation and expansion methods used for the generation of Treg cell lines has significantly interfered with advances in the research on human Treg cells. Thus, there has been a need for methods of producing sufficient number of these Treg cells to permit characterization and to provide for safe and effective therapeutic use in human patients. There has also remained a need for large-scale expansion of human $CD4^+CD25^+$ T cells for clinical trials including, but not limited to immunotherapy or immunosuppression of cancers, particularly solid tumor cancers. Equally important has been a need to suppress in vivo alloresponses and autoimmune responses, such as, although not limited to, graft-vs-host disease (GVHD).

BRIEF SUMMARY OF THE INVENTION

The invention provides a method of generating an inducible T regulatory cell (iTreg). The method comprises contacting a non-Treg with an agent capable of converting the non-Treg into an iTreg, wherein the iTreg is immunosuppressive.

In one embodiment, the agent is selected from the group consisting of a breakdown product of tryptophan, an analog of a metabolic breakdown product of tryptophan, a tryptophan catabolite, a demethylating agent, a histone deacetylase inhibitor (HDACi), an mTOR inhibitor, and any combination thereof.

In another embodiment, the non-Treg is further contacted with TGFβ.

In another embodiment, the non-Treg is selected from the group consisting of CD4+, $CD4^+CD25^-$, $CD4^+CD25^-$ 45RA+ cell, and any combination thereof.

In yet another embodiment, the iTreg is $CD4^+CD25^+$.

In one embodiment, the non-Treg is isolated from a sample obtained from leukopheresis products, bone marrow, lymph tissue, thymus tissue, spleen tissue, or umbilical cord tissue.

In another embodiment, the tryptophan catabolite is kynurenines.

In another embodiment, the mTOR inhibitor is rapamycin.

In one embodiment, the demethylating agent is selected from the group consisting of 5-aza-2'-deoxycitidine (decitibine), 5-Azacytidine, and any combination thereof.

In one embodiment, the HDACi is selected from the group consisting of trichostatin A (TSA), suberoylanilide hydroxamic acid (SAHA), and any combination thereof.

In another embodiment, the method of generating an inducible T regulatory cell (iTreg) further comprises contacting the non-Treg with a bead or artificial antigen-presenting cell (aAPC) expansion system prior to or simultaneously with said agent. In one embodiment, the bead comprises anti-CD3 antibody and anti-CD28 antibody.

In another embodiment, the method of generating an inducible T regulatory cell (iTreg) further comprises contacting the iTreg with a bead or artificial antigen-presenting cell (aAPC) expansion system subsequent to contacting the non-Treg with the agent. In one embodiment, the aAPC comprises an immune stimulatory ligand and at least one co-stimulatory ligand on its surface.

In one embodiment, the stimulatory ligand is a polypeptide selected from the group consisting of a major histocompatibility complex Class I (MHC class I) molecule loaded with an antigen, an anti-CD3 antibody, an anti-CD28 antibody, an anti-CD2 antibody, and any combination thereof.

In another embodiment, the co-stimulatory ligand is selected from the group consisting of CD7, B7-1 (CD80), B7-2 (CD86), PD-L1, PD-L2, 4-1BBL, OX40L, ICOS-L, ICAM, CD30L, CD40, CD70, CD83, HLA-G, MICA, MICB, HVEM, lymphotoxin beta receptor, ILT3, ILT4, 3/TR6, a ligand that specifically binds with B7-H3, and any combination thereof.

The invention provides a method for inhibiting alloreactive T cells. The method comprises contacting alloreactive T cells with an effective amount of iTregs.

The invention provides a method for inhibiting cytotoxic T-lymphocyte (CTL) activity. The method comprises contacting a cytotoxic T-lymphocyte with an effective amount of iTregs.

The invention provides a method for generating an immunosuppressive effect in a mammal having an alloresponse or autoimmune response. The method comprising administering to the mammal an effective amount of iTregs.

In one embodiment, the mammal having an alloresponse or autoimmune response follows tissue transplantation, and wherein the method for generating an immunosuppressive effect in a mammal further comprises suppressing, blocking or inhibiting graft-vs-host disease in the mammal. Preferably, the mammal is a human.

The invention provides a method for preventing an allose-sponse or an autoimmune response in a mammal. The method comprising administering to the mammal, prior to onset of an alloresponse or autoimmune response, an effective amount of iTreg to prevent said response.

In one embodiment, the mammal is treated prior to, at the time of, or immediately after tissue transplantation, and wherein the method further comprises preventing onset of graft-vs-host disease in the mammal.

In one embodiment, the mammal is treated prior to, at the time of, or immediately after tissue transplantation, and wherein the method further comprises blocking rejection of the transplanted tissue in the mammal.

The invention provides a method of treating a transplant recipient to reduce in the recipient an immune response against the transplant. The method comprising administering to a transplant recipient, an effective amount of iTregs to reduce an immune response against the antigen.

In one embodiment, the method of treating a transplant recipient to reduce in the recipient an immune response against the transplant further comprises administering to the recipient an immunosuppressive agent.

In one embodiment, the iTregs are administered to the recipient prior to the transplant, concurrently with the transplant, or subsequent to the transplantation of the transplant.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIG. 1, comprising

FIG. 3, comprising FIG. 3A demonstrates that iTregs (closed), but not T cells primed to TLR activated B cells (open squares), were potently suppressive of a naïve MLR culture. It was observed that iTreg generation was dependent upon the enzyme indoleamine 2,3-dioxygenase (IDO) since IDO inhibition by 1-methyl-trypt (1MT) prevented iTreg conversion (FIG. 3B). FIG. 3C demonstrates that addition of KYN resulted in potent MLR suppression that was not blocked by the addition of 1MT.

FIG. 5, comprising FIG. 5A summarizes the results of culturing $CD4^+CD25^-$ cells in diluent, TSA, TSA/decitibine, or SAHA/decitibine. It was observed in cultures with day 3 TSA or SAHA that addition of decitibine on day 7 (SAHA/decitibine or TSA/decitibine) markedly increased CD4+127loFoxP3hi cells by day 10 from 4.6% (diluent) to 44.5% (SAHA/decitibine), indicating that histone acetylation followed by demethylation was advantageous for iTreg generation (FIG. 5A). No iTreg generation was observed when the cells were cultured in HDACi alone (FIGS. 5B and 5C; SAHA and TSA, respectively), FIG. 5D summarizes the results using 5-Aza-deoxycytidine (decitibine) in a bead- and cell-based antigen-presenting cell system. FIG. 5E summarizes the results using 5-azacytidine in a bead- and cell-based antigen-presenting cell system. FIG. 5F summarizes the results using the combination of an HDACi with a demethylating agent in a bead- and cell-based antigen-presenting cell system.

FIG. 7, comprising FIG. 7A is a flow plot of CD4+ gated cells showing biphasic expression of Foxp3. FIG. 7B is an image summarizing the expression of Foxp3 after treatment with Decitibine in the presence and absence of TGFβ.

FIG. 9, comprising

DETAILED DESCRIPTION

Figure 1A:
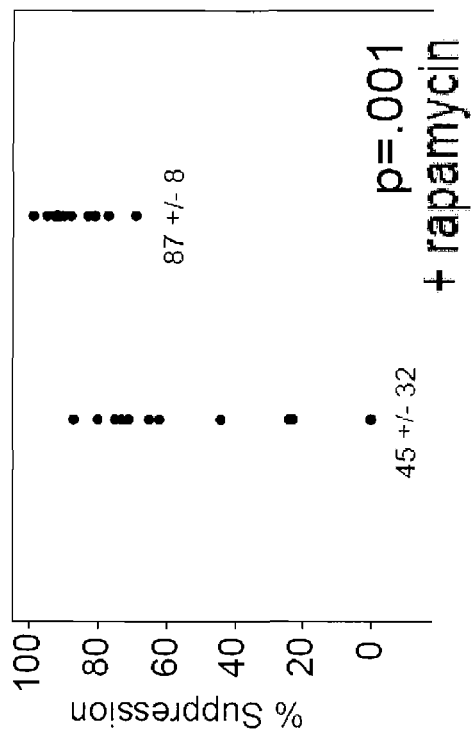
FIGS. 1A and 1B, is a series of charts demonstrating the effects of rapamycin on expansion of $CD4^+CD25^+$ Tregs. Expansion with anti-CD3/28 microbeads in the presence of IL-2 failed to generate uniformly suppressive cells (FIG. 1B). Although anti-CD3 mAb loaded K562 cells modified to express an FcR (CD64) and CD86 (KT64/86) was superior to anti-CD3/28 beads for expanding cells, a high level of suppression was not uniformly observed with either approach (FIG. 1A). Adding rapa (labeled as +) reduced mean expansion rates by 30-fold with beads resulting in ≤10-fold mean expansion rates by day 14. Rapa added to KT64/86 driven cultures (FIG. 1A) reduced mean expansion by 10-fold and improved suppression.

The present invention encompasses compositions and methods for converting non-regulatory T cells (non-Tregs) into Tregs or converting a mixed population of Tregs and non-Tregs into a substantially purified population of Tregs. For example, the invention provides a method of converting $CD4^+CD25^-$ T cells into functional regulatory T cells. The converted cells are referred to as inducible Tregs (iTregs). In one aspect, the iTregs are immunosuppressive.

In addition, the present invention provides a method for enhancing tolerance in a mammalian host to prolong foreign graft survival in the host and for ameliorating inflammatory-related diseases, such as autoimmune diseases, including, but not limited to, autoimmune arthritis, autoimmune diabetes, asthma, septic shock, lung fibrosis, glomerulonephritis, artherosclerosis, as well as AIDS, and the like. In some instances, the iTregs are useful for suppressing an immune response.

The present invention further comprises a method for inhibiting proliferation of a T cell. Such inhibition can occur in vitro or in vivo, preferably in an animal, more preferably in a mammal, even more preferably in a human. This is because, as demonstrated by the data disclosed herein, iTregs converted from non-Tregs according to the methods of the present invention are potent suppressors of T cell proliferation.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

The term "about" will be understood by persons of ordinary skill in the art and will vary to some extent on the context in which it is used.

As used herein, to "alleviate" a disease means reducing the severity of one or more symptoms of the disease.

"Allogeneic" refers to a graft derived from a different animal of the same species.

"Alloantigen" is an antigen that differs from an antigen expressed by the recipient.

The term "antibody" as used herein, refers to an immunoglobulin molecule, which is able to specifically bind to a specific epitope on an antigen. Antibodies can be intact immunoglobulins derived from natural sources or from recombinant sources and can be immunoactive portions of intact immunoglobulins. Antibodies are typically tetramers of immunoglobulin molecules. The antibodies in the present invention may exist in a variety of forms including, for example, polyclonal antibodies, monoclonal antibodies, Fv, Fab and F(ab)$_2$, as well as single chain antibodies and humanized antibodies (Harlow et al., 1988; Houston et al., 1988; Bird et al., 1988).

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

"An antigen presenting cell" (APC) is a cell that is capable of activating T cells, and includes, but is not limited to, monocytes/macrophages, B cells and dendritic cells (DCs).

The term "dendritic cell" or "DC" refers to any member of a diverse population of morphologically similar cell types found in lymphoid or non-lymphoid tissues. These cells are characterized by their distinctive morphology, high levels of surface MHC-class II expression. DCs can be isolated from a number of tissue sources. DCs have a high capacity for sensitizing MHC-restricted T cells and are very effective at presenting antigens to T cells in situ. The antigens may be self-antigens that are expressed during T cell development and tolerance, and foreign antigens that are present during normal immune processes.

The term "autoimmune disease" as used herein is defined as a disorder that results from an autoimmune response. An autoimmune disease is the result of an inappropriate and excessive response to a self-antigen. Examples of autoimmune diseases include, but are not limited to, Addision's disease, alopecia areata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the mammal.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

A "disease" is a state of health of an animal wherein the animal cannot maintain homeostasis, and wherein if the disease is not ameliorated, then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "DNA" as used herein is defined as deoxyribonucleic acid.

"Donor antigen" refers to an antigen expressed by the donor tissue to be transplanted into the recipient.

"Recipient antigen" refers to a target for the immune response to the donor antigen.

As used herein, an "effector cell" refers to a cell which mediates an immune response against an antigen. An example of an effector cell includes, but is not limited to a T cell and a B cell.

"Mixed lymphocyte reaction," "mixed lymphocyte culture," "MLR," and "MLC" are used interchangeably to refer to a mixture comprising a minimum of two different cell populations that are allotypically different. At least one of the allotypically different cells is a lymphocyte. The cells are cultured together for a time and under suitable conditions to result in the stimulation of the lymphocytes, which in this particular invention are Treg cells. A frequent objective of an MLC is to provide allogeneic stimulation, such as may initiate proliferation of the Treg cells; but unless indicated, proliferation during the culture is not required. In the proper context, these terms may alternatively refer to a mixture of cells derived from such a culture. When cells from an MLC are administered as a bolus to a human, it is referred to as a "cellular implant."

As used herein "endogenous" refers to any material from or produced inside an organism, cell, tissue or system.

By the term "effective amount", as used herein, is meant an amount that when administered to a mammal, causes a detectable level of immune suppression or tolerance compared to the immune response detected in the absence of the composition of the invention. The immune response can be readily assessed by a plethora of art-recognized methods. The skilled artisan would understand that the amount of the composition administered herein varies and can be readily determined based on a number of factors such as the disease or condition being treated, the age and health and physical condition of the mammal being treated, the severity of the disease, the particular compound being administered, and the like.

As used herein, the term "exogenous" refers to any material introduced from or produced outside an organism, cell, tissue or system.

The term "epitope" as used herein is defined as a small chemical molecule on an antigen that can elicit an immune response, inducing B and/or T cell responses. An antigen can have one or more epitopes. Most antigens have many epitopes; i.e., they are multivalent. In general, an epitope is roughly about 10 amino acids and/or sugars in size. Preferably, the epitope is about 4-18 amino acids, more preferably about 5-16 amino acids, and even more most preferably 6-14 amino acids, more preferably about 7-12, and most preferably about 8-10 amino acids. One skilled in the art understands that generally the overall three-dimensional structure, rather than the specific linear sequence of the molecule, is the main criterion of antigenic specificity and therefore distinguishes one epitope from another. Based on the present disclosure, a peptide of the present invention can be an epitope.

The term "expression" as used herein is defined as the transcription and/or translation of a particular nucleotide sequence driven by its promoter.

The term "expression vector" as used herein refers to a vector containing a nucleic acid sequence coding for at least part of a gene product capable of being transcribed. In some cases, RNA molecules are then translated into a protein, polypeptide, or peptide. In other cases, these sequences are not translated, for example, in the production of antisense molecules, siRNA, ribozymes, and the like. Expression vectors can contain a variety of control sequences, which refer to nucleic acid sequences necessary for the transcription and possibly translation of an operatively linked coding sequence in a particular host organism. In addition to control sequences that govern transcription and translation, vectors and expression vectors may contain nucleic acid sequences that serve other functions as well.

The term "helper T cell" as used herein is defined as an effector T cell whose primary function is to promote the activation and functions of other B and T lymphocytes and or macrophages. Most helper T cells are CD4 T-cells.

The term "heterologous" as used herein is defined as DNA or RNA sequences or proteins that are derived from the different species.

As used herein, "homology" is used synonymously with "identity."

The term "immunoglobulin" or "Ig", as used herein is defined as a class of proteins, which function as antibodies. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most mammals. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "immunostimulatory" is used herein to refer to increasing overall immune response.

The term "immunosuppressive" is used herein to refer to reducing overall immune response.

"Initiating iTreg conversion" as used herein refers to any event which results in a detectable increase in the phenotype and/or genotype characteristic of regulatory T cells. For example, a phenotype and/or genotype characteristic of regulatory T cell is CD25 expression thus resulting in the generation of $CD4^+CD25^+$ cells from $CD4^+CD25^-$ cells. Another phenotype and/or genotype characteristic of regulatory T cell is immunosuppression.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

The term "polypeptide" as used herein is defined as a chain of amino acid residues, usually having a defined sequence. As used herein the term polypeptide is mutually inclusive of the terms "peptide" and "protein".

The term "self-antigen" as used herein is defined as an antigen that is expressed by a host cell or tissue. Self-antigens may be tumor antigens, but in certain embodiments, are expressed in both normal and tumor cells. A skilled artisan would readily understand that a self-antigen may be overexpressed in a cell.

As used herein, "specifically binds" refers to the fact that a first composition binds preferentially with a second composition and does not bind in a significant amount to other compounds present in the sample.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cells that have been separated from the cells with which they are naturally associated in their natural state. In some embodiments, the cells are culture in vitro. In other embodiments, the cells are not cultured in vitro.

As the term is used herein, "substantially separated from" or "substantially separating" refers to the characteristic of a population of first substances being removed from the proximity of a population of second substances, wherein the population of first substances is not necessarily devoid of the second substance, and the population of second substances is not necessarily devoid of the first substance. However, a population of first substances that is "substantially separated from" a population of second substances has a measurably lower content of second substances as compared to the non-separated mixture of first and second substances.

A "population" is used herein to refer to a group of cells having a substantially similar phenotypic characteristic "Transplant" refers to a biocompatible lattice or a donor tissue, organ or cell, to be transplanted. An example of a transplant may include but is not limited to skin cells or tissue, bone marrow, and solid organs such as heart, pancreas, kidney, lung and liver. A transplant can also refer to any material that is to be administered to a host. For example, a transplant can refer to a nucleic acid or a protein.

The term "T-cell" as used herein is defined as a thymus-derived cell that participates in a variety of cell-mediated immune reactions.

The term "B-cell" as used herein is defined as a cell derived from the bone marrow and/or spleen. B cells can develop into plasma cells which produce antibodies.

As used herein, a "therapeutically effective amount" is the amount of a therapeutic composition sufficient to provide a beneficial effect to a mammal to which the composition is administered.

As used herein, "treating" refers to the reduction, alleviation or elimination, preferably to normal levels, of one or more of the symptoms of the disease or condition which is being treated, e.g. alleviation of immune dysfunction or avoidance of transplant rejection, relative to the symptoms prior to treatment. As used herein "treating" or "treatment" includes both therapeutic and prophylactic treatments.

The term "vaccine" as used herein is defined as a material used to provoke an immune response after administration of the material to a mammal.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Xenogeneic" refers to a graft derived from an animal of a different species.

As used herein, the term "CD127" refers to the alpha subunit of the "interleukin-7 receptor," present on a Treg cell surface. The IL-7 receptor alpha chain is described in the literature. See, e.g., Goodwin et al., 1990 Cell 60:941-951. $CD127^+$ refers to cells which stain intensely or brightly when treated with a labeled antibody directed toward CD127. $CD127^{Lo/-}$ refers to cells of a type which stains slightly/dully or not at all when contacted with a labeled CD127 antibody. Generally, the cells are distinguished according to their CD127 expression levels based upon a readily discernible differences in staining intensity as is known to one of ordinary skill in the art.

As used herein, the term "CD4" refers to a cell-surface glycoprotein typically found on the mature helper T cells and immature thymocytes, as well as on monocytes and macrophages. CD4$^+$ refers to cells which stain brightly when contacted with labeled anti-CD4 antibody, and CD4$^-$ refers to cells of a type which stain the least brightly, dull or not at all, when contacted with a fluorescently labeled CD4 antibody. Generally, the cells are distinguished according to their CD4 expression levels based upon a readily discernible differences in staining intensity as the CD4 staining is clearly bimodal.

As used herein, the term "CD25" refers to the alpha subunit of interleukin-2 receptor, a single-chain glycoprotein with a molecular weight of 55 kD. CD25$^{hi}$ refers to cells which stain brightly when contacted with labeled anti-CD25 antibody, CD25$^+$ refers to cells which stain less brightly when contacted with labeled anti-CD25 antibody, and CD25$^{lo/-}$ refers to cells which are of a type which stains the least brightly, dull or null when contacted with a labeled CD25 antibody. Generally, the cells are distinguished according to their CD25 expression levels based upon differences in staining intensity as is known to one of ordinary skill in the art. In some embodiments, the cut off for designating a cell as a CD25 expression category hi, +, lo, or – cell can be set in terms of the fluorescent intensity distribution observed for all the cells. Generally, cells in the top 2, 3, 4, or 5% of staining intensity are designated "hi", with those falling in the top half of the population categorized as being "+". Those cells falling below 50%, of fluorescence intensity are designated as CD25$^{lo}$ cells and below 5% as CD25$^-$ cells.

Description

The present invention relates to methods and compositions for converting non-regulatory T cells (non-Tregs) into regulatory T cells. For example, the methods include converting CD4+ or CD4$^+$CD25$^-$ into CD4$^+$CD25$^+$ T cells. The constitutive expression of CD25 is considered to be a characteristic feature of Tregs. Thus, Tregs are often CD4$^+$CD25$^+$ T cells, and preferably immunosuppressive. Converted CD4$^+$CD25$^+$ T cells are referred herein as inducible Tregs (iTregs). In some instances, induction of Tregs includes both the generation of Tregs from naïve T cells and the reactivation of quiescent Tregs.

In some instances, the conversion process includes a combinational approach including an initial conversion stage, an outgrowth stage that favors Treg over non-Tregs, and an imprinting stage thereby generating iTregs. The induction of Tregs is associated with the induction of immune tolerance and the suppression of an immune response.

In one embodiment, iTreg conversion includes subjecting non-Tregs to an amino acid starvation environment. For example, initiation of iTreg conversion can be accomplished by exposing non-Tregs with a tryptophan depletion/catabolite.

The present invention also provides a method of reproducing the effects of indoleamine 2,3 dioxygenase (IDO) to induce iTreg conversion by using a downstream tryptophan metabolite, including, but not limited to kynurenin (also referred to herein as "KYN" or "kyn").

In one embodiment, iTreg conversion includes subjecting non-Tregs to a demethylating agent.

In one embodiment, iTreg conversion includes subjecting non-Tregs to a DNA methyltransferase inhibitor.

In some instances, the combinational approach also includes incubating the T cells with an agent that is capable of favoring Treg conversion and outgrowth. An example of such an agent is rapamycin. Rapamycin is an immunosuppressive agent used to prevent allograft rejection. Rapamycin has been shown to selectively expand naturally occurring CD4$^+$CD25$^+$FoxP3$^+$ regulatory T cells. The present invention provides a new protocol using Rapamycin to generate new Treg cells from non-Tregs (e.g., CD4$^+$CD25$^-$ T cells). These inducible Tregs generated in accordance with the methods of the invention exhibit immunosuppressive capacities.

In other instances, the combinational approach also includes incubating non-Tregs with a demethylating agent and histone deacetylace inhibitor (HDACi) for inducing iTregs conversion. In other instances, the approach includes incubating the T cells with a demethylating agent and/or a histone deacetylace inhibitor (HDACi) for imprinting iTregs after the conversion as been initiated.

In some instances, the combinational approach also includes incubating non-Tregs with a demethylating agent (or a DNA methyltransferase inhibitor) and TGFβ for inducing iTregs conversion.

In a preferred aspect, the present invention provides a combinational approach for converting non-Tregs (e.g., CD4$^+$CD25$^-$ T cells) comprising any one or more of the following steps: (i) isolating non-Tregs from a sample (ii) contacting the cells with a) an agent that promotes iTreg conversion, (iii) incubating the cells under conditions to allow proliferation and (iv) isolating the T cells after the incubation.

The invention also provides methods and compositions for ex vivo conversion and expansion of Tregs from non-Tregs. The expansion methods for iTregs generally comprise the use of a bead- or cell-based artificial antigen-presenting cell. However, any method in the art can be used to expand the iTregs.

The present invention provides a method of large-scale conversion and expansion of iTregs that addresses the low numbers of natural Treg cells that can be isolated and expanded. Thus, the methods and compositions of the invention are useful for therapeutic purposes, for example, in the prevention and treatment of immune-based disorders and in the prevention of allograft rejection.

Isolating and Inducible Treg Conversion

Naturally occurring regulatory T (Treg) cells suppress immune responses and play an important role in immunotherapy against autoimmune diseases and provide transplantation tolerance. Various populations of Treg cells have been described and include naturally occurring CD4$^+$CD25$^+$FoxP3$^+$ cells. The natural occurring CD4$^+$CD25$^+$FoxP3$^+$ Treg cells represents about 5-10% of the CD4$^+$ T cells in the peripheral blood and are in a hypoproliferative state which has hampered detailed characterization and the potential use of these cells in a therapeutic setting. It has also been reported that about 1-2% of CD4$^+$ T cells are CD25br natural Tregs in peripheral blood. In vivo uses therefore have relied on expansion protocols to generate sufficient numbers of Treg cells for in vivo use. The clinical use of Treg cells is limited by the lack of appropriate isolation and expansions protocols to generate sufficient numbers for in vivo infusion.

The present invention provides a method of generating a population of immunosuppressive Treg cells from the abundant CD4$^+$CD25$^-$ T cell population. This method allows for the generation of Treg cells in sufficient numbers for in vivo infusions. The method can be used both for generating Treg cells for research purposes and for clinical use by infusion in patients.

In some embodiments, the invention provides for methods of selecting or isolating the cells so identified. In some embodiments, T cells are obtained from blood (e.g., isolated from PBMC), lymphoid, thymus or any specific tissues/organ sample of interest. These tissues or organs would include the pancreas, eye, heart, liver, nerves, intestine, skin, muscle, and joints.

The cells bearing the desired markers can be isolated, for instance, by the use of labeled antibodies or ligands with FACS or magnetic particles/bead technologies as known to one of ordinary skill in the art. Accordingly, in some embodiments, the invention provides a method of generating an isolated population of immunosuppressive regulatory T-cells which are substantially CD4+CD25+ by obtaining a biological sample comprising non regulatory T-cells including, but not limited to, CD4+, CD4+CD25−, CD4+CD25−45RA+ cells, and converting the non regulatory T cells into regulatory T cells or otherwise referred to as inducible T cells (iTregs). In some embodiments, the population of converted inducible T cells is substantially CD4+CD25+ T cells.

Non-Tregs, such as CD4+, CD4+CD25−, and CD4+CD25−45RA+ cells can be isolated by negative selection (e.g., CD8 and CD25). To enhance enrichment of non-Tregs, positive selection may be combined with negative selection against cells comprising surface makers specific to non-Treg cell types, CD11b, CD16, CD19, CD36 and CD56-bearing cells. Preferably, a positive marker for positive selection is 45RA. As a non-limiting example, CD4+CD25−45RA+ cells can initially be isolated by negative selection (e.g., CD8 and CD25). To enhance enrichment of CD4+CD25−45RA+ cells, positive selection may be combined with negative selection against cells comprising surface maker 45RA.

Sources of T cells and methods of isolating particular T cell populations (e.g. CD4+ cells) which can be converted by stimulation according to the methods of the present invention are well known and described in the literature. Thus for example T cells may conveniently be isolated from the blood e.g. from a peripheral blood mononuclear cell (PBMC) population isolated from blood, or from other blood-derived preparations such as leukopheresis products or from bone marrow, lymph, thymus, spleen or umbilical cord. T cell populations may be derived from any appropriate source, including human or animal sources.

The present invention also includes a combinational approach of generating regulatory T cells (Tregs) in vitro. The method includes obtaining non-Tregs (e.g., CD4+CD25− cells) or mixed populations of Tregs and non-Tregs from a subject and converting the non-Tregs into inducible Tregs. Converting non-Tregs into iTregs includes at least one or more of the following stages: a stage of initiating the iTreg conversion process; a stage to favor Treg conversion and outgrowth; and a stage for imprinting iTregs after conversion has been initiated. Any expansion method can be used in conjunction with the combinational approach of the present invention. For example, a bead- or cell-based artificial antigen-presenting cell system can be used before, during, and/or after any of the stages included in the combinational approach of generating Tregs.

Initiation Stage:

It has been shown that cells expressing the tryptophan-catabolizing enzyme, indoleamine 2,3-dioxygenase (IDO), are capable of inhibiting T cell proliferation in vitro and reducing T cell immune responses in vivo. The immunosuppressive effect of IDO can be blocked by the in vivo administration of an IDO inhibitor, such as 1-methyl-tryptophan (also referred to herein as 1-MT or IMT). IDO degrades the essential amino acid tryptophan. IDO is the first and rate-limiting step in the degradation of tryptophan to the downstream metabolite kynurenine (KYN) and subsequent metabolites along the KYN pathway. The results presented herein demonstrate that conversion of non-Tregs into Tregs is partly attributable to the biological activity of IDO, where the conversion process is partly dependent on the ability of IDO to catabolize tryptophan. Therefore, the present invention is partly based on IDO-mediated production of metabolites in the KYN pathway as the exemplary mechanism of Treg generation by the combinational approach of the invention.

The present invention demonstrates that IDO expression contributes to the generation of CD4+ Tregs and demonstrates that this effect can be pharmacologically reproduced by the addition of a metabolic breakdown product of tryptophan, or an analog of a metabolic breakdown product of tryptophan. Tryptophan is also referred to herein as "Tryp," "tryp," "Trp" or "trp."

The present invention includes methods of initiating conversion of non-Tregs into Tregs or otherwised referred to as inducible Tregs. The method includes contacting non-Tregs with a metabolic breakdown product of tryptophan, or an analog of a metabolic breakdown product of tryptophan. This stage of the combinational approach of the invention includes for example incubating CD4+ cells (non Tregs) in tryptophan depletion conditions for a time sufficient to induce the convesion of non-Tregs to Tregs. In some instances, the conversion process includes induction of a stress response. Preferably, a stress response is created by contacting non Tregs with trypt for a period of time followed by culturing the cells in additional permissive growth conditions. In some instances, permissive growth conditions can be created using tyrpt and/or typt metabolites. Preferably, the permissive condition is the combination of low concentrations of trypt and KYN (trypt/KYN).

The metabolic breakdown product of tryptophan, or an analog of a metabolic breakdown product of tryptophan, may be contacted with non-Tregs in an amount effective to induce IDO expression. The results presented herein demonstrate that induced IDO activity stimulates conversion of non-Tregs (e.g., CD4+CD25−) into Tregs to acquire increased T cell suppressor functions. It is also believed that IDO activity stimulates rapid increase of Treg suppressor functions and activates the GCN2 stress response selectively in Tregs. The combined effects of Trp depletion and Trp catabolites induces non Tregs to acquire a regulatory phenotype, and that this mechanism is believed to be mediated by GCN2. The protein kinase GCN2 is also referred to as "General Control Nonderepressible 2," "eIF2AK4," and "eukaryotic translation initiation factor 2 alpha kinase 4".

The present invention includes the use of a metabolic breakdown product of tryptophan, or an analog of a metabolic breakdown product of tryptophan, for the generation of Tregs. As used herein, an "analog" refers to a chemical compound or molecule made from a parent compound or molecule by one or more chemical reactions. As such, an analog can be a compound with a structure similar to or based on that of a metabolic breakdown product of tryptophan, but differing from it in respect to certain components or structural makeup, which may have a similar action metabolically. In preferred embodiments, the metabolic breakdown product of tryptophan is L-kynurenine, kynurenic acid, anthranilic acid, 3-hydroxyanthranilic acid, quinolinic acid, or picolinic acid, and an analog of a metabolic breakdown product of tryptophan is an analog of L-kynurenine, kynurenic acid, anthranilic acid, 3-hydroxyanthranilic acid, quinolinic acid, or picolinic acid.

Another approach to initiate the iTreg conversion process is to expose non-Tregs with a demethylating agent or an inhibitor of DNA methylation. This is because contrary to non-Tregs, natural Tregs are hypomethylated and it has been observed that complete demethylation and histone modifications occur in the FoxP3 locus of natural Tregs. Therefore, exposing non-Tregs to a demethylating agent would alter the chromosomal structure of the non-Tregs in a manner that renders the non-Tregs more suseptiable for iTreg conversion. It is believed that exposing non-Tregs to a demethylating agent, such as 5-aza-2'-deoxycitidine (decitibine) or 5-Azacytidine induces significant expression of FOXP3 and thereby initiates the conversion of non Tregs into Tregs. Without wishing to be bound by any particular theory, decitibine is also considered to be a DNA methyltransferase inhibitor.

Another approach to initiate the iTreg conversion process is to expose non-Tregs with a combination of a demethylation agent (or a DNA methyltransferase inhibitor) and a histone deacetylase inhibitor (HDACi).

Another approach to initiate the iTreg conversion process is to expose non-Tregs with a combination of a demethylation agent (or a DNA methyltransferase inhibitor) and TGFβ.

Conversion and Outgrowth Stage:

Rapamycin (Rapa) is an immunosuppressive agent used to prevent allograft rejection. The cellular target for Rapamycin in vitro has been discovered, and was shown to selectively expand naturally occurring regulatory T cells (e.g., $CD4^+CD25^+FoxP3^+$). The present invention relates to a combiantional approach of converting non-Tregs into Tregs (referred to as inducible Tregs; iTregs) using Rapamycin in combination with other agents and methods discussed elsewhere herein to optimize the conversion and large-scale expansion of iTregs. This is because the results presented herein demonstrate that Rapa can be used to promote selective outgrowth of Tregs over non-Tregs.

Rapa, an mTOR (mammalian target of rapamycin) inhibitor, has been shown to suppress non-Tregs and favor iTreg conversion. mTOR is a member of the PIK-related family of large protein kinases and mediates the phosphorylation of at least two regulators of protein synthesis and cell growth: S6 Kinase 1 (S6K1) and an inhibitor of translation initiation, the eIF-4E binding protein 1 (4E-BP1). mTOR is an important signaling intermediate molecule downstream of the PI3K/AKT pathway that inhibits apoptosis, and is important in nutritional status checkpoint, mTOR is a large multidomain serine/threonine kinase, and is a member of the PI3K family of protein kinases based on homology within its catalytic domain. It has been shown that natural Tregs are less dependent than non-Tregs on the mTOR/Akt pathway. Therefore, exposing non-Tregs to Rapa favors iTregs and natural Tregs due to the dependency of non-Tregs on mTOR/p-Akt for proliferation and survival. Accordingly, the invention includes the use of any mTOR inhibitor to selectively favor the outgrowth of iTregs and/or natural Tregs over non-Tregs.

Mammalian target of rapamycin ("mTOR") regulates the activity of at least two proteins involved in the translation of specific cell cycle regulatory proteins. One of these proteins, p70s6 kinase, is phosphorylated by mTOR on serine 389 as well as threonine 412. This phosphorylation can be observed in growth factor treated cells by Western blotting of whole cell extracts of these cells with antibody specific for the phosphoserine 389 residue. As used herein, the term "mTOR inhibitor" means a compound or ligand which inhibits cell replication by blocking progression of the cell cycle from G1 to S by inhibiting the phosphorylation of serine 389 of p70s6 kinase by mTOR. One skilled in the art can readily determine if a compound, such as a rapamycin derivative, is an mTOR inhibitor.

As used herein, the term "rapamycin derivatives" includes compounds having the rapamycin core structure as defined in U.S. patent application Publication No. 2003/0008923, which may be chemically or biologically modified while still retaining mTOR inhibiting properties. Such derivatives include esters, ethers, oximes, hydrazones, and hydroxylamines of rapamycin, as well as compounds in which functional groups on the rapamycin core structure have been modified, for example, by reduction or oxidation. Pharmaceutically acceptable salts of such compounds are also considered to be rapamycin derivatives.

Specific examples of esters and ethers of rapamycin are esters and ethers of the hydroxyl groups at the 42- and/or 31-positions of the rapamycin nucleus, and esters and ethers of a hydroxyl group at the 27-position (following chemical reduction of the 27-ketone). Specific examples of oximes, hydrazones, and hydroxylamines are of a ketone at the 42-position (following oxidation of the 42-hydroxyl group) and of 27-ketone of the rapamycin nucleus.

Examples of 42- and/or 31-esters and ethers of rapamycin are disclosed in the following patents, which are hereby incorporated by reference in their entireties: alkyl esters (U.S. Pat. No. 4,316,885); aminoalkyl esters (U.S. Pat. No. 4,650,803); fluorinated esters (U.S. Pat. No. 5,100,883); amide esters (U.S. Pat. No. 5,118,677); carbamate esters (U.S. Pat. No. 5,118,678); silyl ethers (U.S. Pat. No. 5,120,842); aminoesters (U.S. Pat. No. 5,130,307); acetals (U.S. Pat. No. 551,413); aminodiesters (U.S. Pat. No. 5,162,333); sulfonate and sulfate esters (U.S. Pat. No. 5,177,203); esters (U.S. Pat. No. 5,221,670); alkoxyesters (U.S. Pat. No. 5,233,036); O-aryl, -alkyl, -alkenyl, and -alkynyl ethers (U.S. Pat. No. 5,258,389); carbonate esters (U.S. Pat. No. 5,260,300); arylcarbonyl and alkoxycarbonyl carbamates (U.S. Pat. No. 5,262,423); carbamates (U.S. Pat. No. 5,302,584); hydroxyesters (U.S. Pat. No. 5,362,718); hindered esters (U.S. Pat. No. 5,385,908); heterocyclic esters (U.S. Pat. No. 5,385,909); gem-disubstituted esters (U.S. Pat. No. 5,385,910); amino alkanoic esters (U.S. Pat. No. 5,389,639); phosphorylcarbamate esters (U.S. Pat. No. 5,391,730); carbamate esters (U.S. Pat. No. 5,411,967); carbamate esters (U.S. Pat. No. 5,434,260); amidino carbamate esters (U.S. Pat. No. 5,463,048); carbamate esters (U.S. Pat. No. 5,480,988); carbamate esters (U.S. Pat. No. 5,480,989); carbamate esters (U.S. Pat. No. 5,489,680); hindered N-oxide esters (U.S. Pat. No. 5,491,231); biotin esters (U.S. Pat. No. 5,504,091); O-alkyl ethers (U.S. Pat. No. 5,665,772); and PEG esters of rapamycin (U.S. Pat. No. 5,780,462).

Examples of 27-esters and ethers of rapamycin are disclosed in U.S. Pat. No. 5,256,790, which is hereby incorporated by reference in its entirety.

Examples of oximes, hydrazones, and hydroxylamines of rapamycin are disclosed in U.S. Pat. Nos. 5,373,014, 5,378,836, 5,023,264, and 5,563,145, which are hereby incorporated by reference. The preparation of these oximes, hydrazones, and hydroxylamines is disclosed in the above listed patents. The preparation of 42-oxorapamycin is disclosed in U.S. Pat. No. 5,023,263, which is hereby incorporated by reference.

Other compounds within the scope of "rapamycin derivatives" include those compounds and classes of compounds referred to as "rapalogs" in, for example, WO 98/02441 and references cited therein, and "epirapalogs" in, for example, WO 01/14387 and references cited therein, the disclosures of which are incorporated herein by reference in their entireties.

Another compound within the scope of "rapamycin derivatives" is everolimus, a 4-O-(2-hydroxyethyl)-rapamycin derived from a macrolide antibiotic produced by *Streptomyces hygroscopicus* (Novartis). Everolimus is also known as Certican, RAD-001 and SDZ-RAD.

Another preferred mTOR inhibitor is tacrolimus, a macrolide lactone immunosuppressant isolated from the soil fungus *Streptomyces tsukubaensis*, Tacrolimus is also known as FK 506, FR 900506, Fujimycin, L 679934, Tsukubaenolide, Protopic and Prograf.

Another preferred mTOR inhibitor is ABT-578 an antiproliferative agent (Abbott Laboratories). ABT-578 is believed to inhibit smooth muscle cell proliferation with a cytostatic effect resulting from the inhibition of mTOR.

Other preferred mTOR inhibitors include AP-23675, AP-23573, and AP-23841 (Ariad).

Preferred rapamycin derivatives include everolimus, CCI-779 [rapamycin 42-ester with 3-hydroxy-2-(hydroxymethyl)-2-methylpropionic acid; U.S. Pat. No. 5,362,718]; 7-epi-rapamycin; 7-thiomethyl-rapamycin; 7-epi-trimethoxyphenyl-rapamycin; 7-epi-thiomethyl-rapamycin; 7-demethoxy-rapamycin; 32-demethoxy-rapamycin; 2-desmethyl-rapamycin; and 42-O-(2-hydroxy)ethyl rapamycin (U.S. Pat. No. 5,665,772).

By way of a non-limiting example, Rapamycin is contacted with the desired cells prior to, simultaneously with, and/or subsequent to exposing the cells to conditions that initiate iTreg conversion. For example, Rapa is contacted with the desired cells prior to, simultaneously with, and/or subsequent to exposing non-Treg cells to amino acid depletion conditions such as trypt depletion conditions. In some instances, Rapa is contacted with the desired cells prior to, simultaneously with, and/or subsequent to exposing non-Treg cells to amino acid depletion conditions such as trypt depletion/catabolites and/or a demethylating agent whereby the amino acid depletion conditions and/or demethylating agent initiates iTreg conversion. In other instances, Rapa is contacted with the desired cells prior to, simultaneously with, and/or subsequent to exposing non-Treg cells to a combination of a demethylating agent and a HDACi.

Rapamycin may be used at a concentration of from about 0.01 μM to about 10 μM, such as about 0.5 μM to about 2 μM, or about 1 μM.

It is also believed that the mTOR pathway is particularly sensitive to the levels of nutrients, such as amino acids. Therefore, without wishing to be bound by any particular theory, it is believed that exposing non-Tregs to an amino acid starvation environment such as Crypt depletion/catabolites (e.g., low trypt/KYN) contributes to the regulation of the mTOR pathway.

Imprinting Stage:

An emerging paradigm in understanding the development of stable cellular lineages emphasizes the role of epigenetic mechanisms for the permanent, heritable fixation of distinct gene expression patterns. Molecular mechanisms of epigenetic imprinting include selective demethylation of CpG motifs and histone modifications. It is believed that iTreg conversion involves elements of epigenetic alterations such as DNA methylation and histone modifications of at least the foxp3 loci correlate with Foxp3. The present invention is partly based on the observation that the selective association of chromatin remodelling with a stable Treg phenotype establishes a role of epigenetic imprinting in the establishment of a committed regulatory T cell type.

Histone deacetylases (HDACs) regulate chromatin remodeling and gene expression as well as the functions of a number of transcription factors and nonhistone proteins. The results presented herein demonstrate that a histone deacetylase inhibitor (HDACi) allows for the beneficial enhancement of converting non-Tregs into Tregs.

It has been shown that HDACi treatment enhances the production of Treg cells by either increasing thymic output of Treg cells or peripheral conversion of conventional T cells (non-Treg cells) into Treg cells. HDAC is are known to increase histone acetylation, resulting in chromatin remodelling and modulation of gene transcription. HDACi therapy also increases expression of Treg-associated gene such as Foxp3.

Suberoylanilide hydroxamic acid (SAHA) and trichostatin A (TSA) target class I and II HDACs, respectively. HDAC7 is affected by vorinostat and HDAC9 by TSA; both class IIa HDACs have been linked to FoxP3 regulation (Tao et al., 2007, Nat Med 13:1299-307; Dokmanovic et al., 2007, Mol Cancer Ther 6:2525-34). In a preferred embodiment, an HDACi is used in conjunction with a demethylation agent to generate iTregs. An example of a demethylating agent is 5-aza-2'-deoxycitidine (decitibine) or 5-Azacytidine. Without wishing to be bound by any particular theory, it is believed that histone acetylation followed by demethylation is advantageous for iTreg generation. For example, non-Tregs can be incubated with a combination of TSA/decitibine or SAHA/decitibine treatment for iTreg conversion.

Therefore, the invention includes a method of exposing non-Tregs to any combination of an amino acid depletion condition, a tryptophan depletion/catabolite, a demethylating agent, a DNA methyltransferase inhibitor, an HDACi, and an inhibitor of mTOR (e.g., rapamycin), TGF-β to convert the non-Tregs into Tregs.

In some instances, the invention provides a combinational approach to convert non-Tregs into Tregs or otherwise generate iTregs. The combinatorial approach includes an initial conversion stage, an outgrowth stage that favors proliferation of Tregs, and an imprinting stage. In one embodiment, generation of iTregs involves exposing non-Tregs to an amino acid starvation environment, including but is not limited to a trypt depletion/catabolite condition (e.g., Low tryp/KYN), a demethylating agent (e.g., decitibine), or a combination of a demethylating agent with a HDACi to initiate the iTreg conversion process. To promote outgrowth of the converted Tregs, rapa or a mTOR inhibitor can be added to the cells to favor Treg conversion and outgrowth. To promote imprinting of iTregs, a demethylating agent and/or HDACi can be added to the cell culture. In some instances, the iTregs are imprinted after conversion has been initiated, Expansion:

The invention includes converting non-Tregs or mixed populations of Tregs and non-Tregs into Tregs in the presence of a bead- or cell-based artificial antigen-presenting cell system. Cells can be expanded using a bead- or cell-based artificial antigen-presenting cell system. Regardless of the system used for cellular expansion, the cells can be expanded prior to, simultaneously with, and/or subsequent to iTreg conversion. For example, the cells can be expanded using a bead- or cell-based artificial antigen-presenting cell system before the initial iTreg conversion stage. Alternatively, the cells can be expanded using a bead- or cell-based artificial antigen-presenting cell system after the initial iTreg conversion stage but before the selective outgrowth stage that favors proliferation of Tregs. Alternatively, the cells can be expanded using a bead- or cell-based artificial antigen-presenting cell system after the outgrowth stage but before the imprinting stage. Alternatively, the cells can be expanded using a bead- or cell-based artificial antigen-presenting cell system after the imprinting state.

Special cell-sized beads (e.g., magnetic iron-dextran beads) are used that are coated with antibodies to CD3 and CD28. The anti-CD28 provides critical signals for augmented activation and growth of the hypo-proliferative Treg cells. The use of anti-CD3/anti-CD28 beads induced robust proliferation of suppressor cells, having the effect of plastic-bound antibody. CD28 stimulation also enhances the activation of Treg cells and a present embodiment shows that beads coated with anti-CD3 and anti-CD28 (anti-CD3/CD28) antibody mixed with Treg cells at various ratios. As a non-limiting example, a 3:1 bead:T cell ratio expands and preserves Treg function at a desirable level. CD28 is a disulfide bonded homodimer, expressed on the surface of the majority of T cells (June et al., Immunol Today 11:211 (1990)). CD28 can be identified by a number of commercially available CD28 monoclonal antibodies, as would be known to one of skill in the art. The ratios of antibodies to CD3 and CD28 can be adjusted for optimal results. The beads can easily be removed by passing the cultured cells through a magnetic column. As an added advantage, the culture-expanded iTregs retain potent functional suppressor activity.

The present invention includes converting non-Tregs and mixed populations of non-Tregs and Tregs into Tregs in a cell-based artificial antigen presenting cell (aAPC) expansion system. In a non-limiting example, cell-based aAPCs were created by electroporation of K562 cells with CD32 and 4-1BBL expression plasmids. Using a combination of drug selection, cell sorting, and limiting dilution, high-expressing clones were isolated (Maus et al., 2002, Nature Biotechnol. 20:143-148).

A cell-based aAPC was designed to enable genetic manipulation of the expression of different costimulatory molecules for the long term growth of T cells. The culture system was based on the fact that costimulatory signals, in addition to those provided by CD28, are required for optimal CD8 cell growth. The human erythromyeloid CML cell line K562 (Lozzio et al., 1975, Blood 45:321-334) was used as a scaffold for the cellular aAPCs, because this cell line does not express HLA proteins that would promote allogeneic responses. However, K562 do express ICAM (CD54) and LFA-3 (CD58), both of which promote interactions with T cell. Other advantages of using K562 cell include, but are not limited to, the fact that irradiated K562 cells can be introduced in the clinical setting as these cells are mycoplasma-free, propagate in serum-free medium, and are easily killed by natural killer (NK) cells.

The aAPC is engineered to have on its surface at least one molecule capable of binding to a T-lymphocyte and inducing a primary activation event and/or a proliferative response or capable of binding a molecule having such an affect thereby acting as a scaffold. For example, the aAPC is engineered to express a molecule that binds to the Fc portion of an antibody. In some instances, the aAPC is engineered to stably express a molecule capable of binding to the Fc portion of an antibody. The aAPC can then be loaded or otherwise coated with or have attached thereto any variety of antibodies that recognize cell surface molecules present on the surface of T lymphocytes, e.g., CD3, or a component of the TCR/CD3 complex, CD28, 4-1BB, TCR, etc. Alternatively, the aAPC can be generated by directly engineering a cell line to stably express the ligands for cell surface molecules present on the surface of T lymphocytes, e.g. CD3, or a component of the TCR/CD3 complex, CD28, 4-1BB, TCR, etc. The aAPC can be further engineered to stably express one or more co-stimulatory molecules, for example CD86 or 4-1BB ligand. In a non-limited example, an aAPC is engineered to express the human low-affinity Fcγ receptor, CD32 and the CD86 molecule. In another illustrative example, the aAPC is engineered to express CD32 and the 4-1BB ligand. In one embodiment, the aAPC can be generated to express membrane bound ScFv or a fragment thereof, that recognize any cell surface molecule of interest, such as CD3, CD28, 41BB and the like, or that recognize other antibodies, such as through binding to the Fc portion. In this regard, the aAPC can be armed with secondary antibodies that bind through recognition of the Fc portion. The skilled artisan would readily recognize that any variety and combination of stimulatory and/or co-stimulatory molecules can be used in the context of the present invention.

The skilled artisan would appreciate, based upon the disclosure provided herein, that numerous immunoregulatory molecules can be used to produce an almost limitless variety of aAPCs. For example, a primary signal, usually mediated via the T cell receptor/CD3 complex on a T cell, initiates the T cell activation process. Additionally, numerous co-stimulatory molecules present on the surface of a T cell are involved in regulating the transition from resting T cell to cell proliferation. Such co-stimulatory molecules, also referred to as "co-stimulators", which specifically bind with their respective ligands, include, but are not limited to, CD28 (which binds with B7-1 [CD80], B7-2 [CD86]), PD-1 (which binds with ligands PD-L1 and PD-L2), B7-H3, 4-1BB (binds the ligand 4-1BBL), OX40 (binds ligand OX40L), ICOS (binds ligand ICOS-L), and LFA (binds the ligand ICAM). Thus, the primary stimulatory signal mediates T cell stimulation, but the co-stimulatory signal is then required for T cell activation, as demonstrated by proliferation.

K562 cells can be transduced, either serially and/or in parallel, with a wide plethora of exogenous nucleic acids to express a number of molecules thereby obtaining a library of aAPCs with desired phenotypes. With regard to use of K562 to produce aAPCs, the disclosures of U.S. patent application Ser. No. 10/336,135 (now published as U.S. Patent Application Publication No, US2003/0147869A1) and International Patent Application No. PCT/US03/00339 (now published as International Publication No. WO 03/057171A2) are incorporated by reference as if set forth in their entirety herein.

The culture-expanded iTregs of the present invention are capable of suppressing an MLR, either with fresh $CD4^+$ cells or cultured $CD4^+CD25^-$ cells as responding T cells. In one embodiment the converted and expanded iTregs inhibit the autologous proliferation of peripheral blood cells. In another embodiment, the converted and expanded iTregs block or prevent GVHD, or inhibit or reverse the disease if already in progress. In yet another embodiment, the converted and expanded cells are introduced into a different host; whereas in yet another embodiment, the iTregs are established as a cell line for continuous therapeutic use. Preferably, the host is a human host and the culture-expanded iTregs are human, although animals, including animal models for human disease states, are also included in this invention and therapeutic treatments of such animals are contemplated herein.

Following iTreg conversion using the methods of the invention, Tregs and iTregs can be expanded under appropriate conditions for growth of the Tregs cells. Growth is allowed to progress for a time period selected according to the final number of T cells required and the rate of expansion of the cells. Passaging of the cells may be undertaken during this period. Such a time period is normally between 3 and 10 days but can be as long as 14 to 20 days or even longer providing the viability and continued proliferation of the T cells is maintained.

Therapeutic Application

The invention includes a method of suppressing an immune response in a mammal for the treatment or prevention of an autoimmune condition or transplantation rejection. The ex vivo culture-converted and culture-expanded iTregs with or without natural Tregs may be reintroduced to the host or to another patient by a number of approaches. Preferably, they are injected intravenously. Optionally, the host may be treated with agents to promote the in vivo function and survival of the stimulated cells. Of course, the culture-expanded iTregs may also be reintroduced in a variety of pharmaceutical formulations. These may contain such normally employed additives as binders, fillers, carriers, preservatives, stabilizing agents, emulsifiers, and buffers. Suitable diluents and excipients are, for example, water, saline, and dextrose, as utilized in the methods described below.

This method thus provides a method of achieving an immunosuppressive effect in a mammal, i.e. a method of preventing an immune response. The condition or disease typified by an aberrant immune response may be an autoimmune disease, for example diabetes, multiple sclerosis, myasthenia gravia, neuritis, lupus, rheumatoid arthritis, psoriasis or inflammatory bowel disease. Conditions in which immune suppression would be advantageous include conditions in which a normal or an activated immune response is disadvantageous to the mammal, e.g. allotransplantation of e.g. body fluids or parts, to avoid rejection, or in fertility treatments in which inappropriate immune responses have been implicated in failure to conceive and miscarriage. The use of such cells before, during, or after transplantation avoids extensive chronic graft versus host disease which may occur in patients being treated (e.g. cancer patients). The cells may be converted immediately after harvest or stored (e.g. by freezing) prior to expansion or after expansion and prior to their therapeutic use. The therapies may be conducted in conjunction with known immunosuppressive therapies.

The methods of the present invention are particularly useful for humans, but may also be practiced on veterinary subjects. An "individual," "subject," "patient" or "host" referred to herein is a vertebrate, preferably a mammal. More preferably, such individual is a human and the culture-expanded cells are human, although animals, including animal models for human disease states, are also included in this invention and therapeutic treatments of such animals are contemplated herein. Such animal models can be used to test and adjust the compositions and methods of this invention, if desired. Certain models involve injecting in-bred animals with established cell populations. Also useful are chimeric animal models, described in U.S. Pat. Nos. 5,663,481, 5,602,305 and 5,476,993; EP application 379,554; and International Appl. WO 91/01760. Non-human mammals include, but are not limited to, veterinary or farm animals, sport animals, and pets. Accordingly, as opposed to animal models, such animals may be undergoing selected therapeutic treatments.

The present invention encompasses a method of reducing and/or eliminating an immune response to a transplant in a recipient by administering to the recipient of the transplant an amount of iTregs effective to reduce or inhibit host rejection of the transplant. Without wishing to be bound to any particular theory, the iTregs that are administered to the recipient of the transplant inhibit the activation and proliferation of the recipient's T cells or induce tolerance.

The transplant can include a biocompatible lattice or a donor tissue, organ or cell, to be transplanted. An example of a transplant may include but is not limited to skin cells or tissue, bone marrow, and solid organs such as heart, pancreas, kidney, lung and liver. In some instances, the transplant is a nucleic acid or a protein.

Based upon the disclosure provided herein, iTregs can be obtained from any source, for example, from the tissue donor, the transplant recipient or an otherwise unrelated source (a different individual or species altogether). The iTregs may be autologous with respect to the T cells (obtained from the same host) or allogeneic with respect to the T cells. In the case where the iTregs are allogeneic, the iTregs may be autologous with respect to the transplant to which the T cells are responding to, or the iTregs may be obtained from a mammal that is allogeneic with respect to both the source of the T cells and the source of the transplant to which the T cells are responding to. In addition, the iTregs may be xenogeneic to the T cells (obtained from an animal of a different species), for example rat iTregs may be used to suppress activation and proliferation of human T cells.

Another embodiment of the present invention encompasses the route of administering iTregs to the recipient of the transplant. iTregs can be administered by a route which is suitable for the placement of the transplant, i.e. a biocompatible lattice or a donor tissue, organ or cell, nucleic acid or protein, to be transplanted. iTregs can be administered systemically, i.e., parenterally, by intravenous injection or can be targeted to a particular tissue or organ, such as bone marrow. iTregs can be administered via a subcutaneous implantation of cells or by injection of the cells into connective tissue, for example, muscle.

Tregs can be suspended in an appropriate diluent, at a concentration of about $5 \times 10^6$ cells/ml. Suitable excipients for injection solutions are those that are biologically and physiologically compatible with the Tregs and with the recipient, such as buffered saline solution or other suitable excipients. The composition for administration can be formulated, produced and stored according to standard methods complying with proper sterility and stability.

The dosage of the Tregs varies within wide limits and may be adjusted to the mammal requirements in each particular case. The number of cells used depends on the weight and condition of the recipient, the number and/or frequency of administrations, and other variables known to those of skill in the art.

Between about $10^5$ and about $10^{13}$ Tregs per 100 kg body weight can be administered to the mammal. In some embodiments, between about $1.5 \times 10^6$ and about $1.5 \times 10^{12}$ cells are administered per 100 kg body weight. In some embodiments, between about $1 \times 10^9$ and about $5 \times 10^{11}$ cells are administered per 100 kg body weight. In some embodiments, between about $4 \times 10^9$ and about $2 \times 10^{11}$ cells are administered per 100 kg body weight. In some embodiments, between about $5 \times 10^8$ cells and about $1 \times 10^{10}$ cells are administered per 100 kg body weight.

In another embodiment of the present invention, Tregs are administered to the recipient prior to, or contemporaneously with a transplant to reduce and/or eliminate host rejection of the transplant. While not wishing to be bound to any particular theory, Tregs can be used to condition a recipient's immune system to the transplant by administering Tregs to the recipient, prior to, or at the same time as transplantation of the transplant, in an amount effective to reduce, inhibit or eliminate an immune response against the transplant by the recipient's T cells. The Tregs affect the T cells of the recipient such that the T cell response is reduced, inhibited or eliminated when presented with the transplant. Thus, host rejection of the transplant may be avoided, or the severity thereof reduced, by administering Tregs to the recipient, prior to, or at the same time as transplantation.

In yet another embodiment, Tregs can be administered to the recipient of the transplant after the administration of the transplant. Further, the present invention comprises a method of treating a patient who is undergoing an adverse immune response to a transplant by administering Tregs to the patient in an amount effective to reduce, inhibit or eliminate the immune response to the transplant, also known as host rejection of the transplant.

Therapy to Inhibit Adverse Immune Responses Following Transplantation

The present invention includes a method of using Tregs as a therapy to inhibit graft versus host disease or graft rejection following transplantation. Accordingly, the present invention encompasses a method of contacting a donor transplant, for example a biocompatible lattice or a donor tissue, organ or cell, with Tregs prior to transplantation of the transplant into a recipient. The Tregs serve to ameliorate, inhibit or reduce an adverse response by the donor transplant against the recipient.

As discussed elsewhere herein, Tregs can be obtained from any source, for example, from the tissue donor, the transplant recipient or an otherwise unrelated source (a different individual or species altogether) for the use of eliminating or reducing an unwanted immune response by a transplant against a recipient of the transplant. Accordingly, Tregs can be autologous, allogeneic or xenogeneic to the tissue donor, the transplant recipient or an otherwise unrelated source.

In an embodiment of the present invention, the transplant is exposed to Tregs prior, at the same time, or after transplantation of the transplant into the recipient. In this situation, an immune response against the transplant caused by any alloreactive recipient cells would be suppressed by the Tregs present in the transplant. The Tregs are allogeneic to the recipient and may be derived from the donor or from a source other than the donor or recipient. In some cases, Tregs autologous to the recipient may be used to suppress an immune response against the transplant. In another case, the Tregs may be xenogeneic to the recipient, for example mouse or rat Tregs can be used to suppress an immune response in a human. However, it is preferable to use human Tregs in the present invention.

In another embodiment of the present invention, the donor transplant can be "preconditioned" or "pretreated" by treating the transplant prior to transplantation into the recipient in order to reduce the immunogenicity of the transplant against the recipient, thereby reducing and/or preventing graft versus host disease or graft rejection. The transplant can be contacted with cells or a tissue from the recipient prior to transplantation in order to activate T cells that may be associated with the transplant. Following the treatment of the transplant with cells or a tissue from the recipient, the cells or tissue may be removed from the transplant. The treated transplant is then further contacted with Tregs in order to reduce, inhibit or eliminate the activity of the T cells that were activated by the treatment of the cells or tissue from the recipient. Following this treatment of the transplant with Tregs, the Tregs may be removed from the transplant prior to transplantation into the recipient. However, some Tregs may adhere to the transplant, and therefore, may be introduced to the recipient with the transplant. In this situation, the Tregs introduced into the recipient can suppress an immune response against the recipient caused by any cell associated with the transplant. Without wishing to be bound to any particular theory, the treatment of the transplant with Tregs prior to transplantation of the transplant into the recipient serves to reduce, inhibit or eliminate the activity of the activated T cells, thereby preventing restimulation, or inducing hyporesponsiveness of the T cells to subsequent antigenic stimulation from a tissue and/or cells from the recipient. One skilled in the art would understand based upon the present disclosure, that preconditioning or pretreatment of the transplant prior to transplantation may reduce or eliminate the graft versus host response.

For example, in the context of umbilical cord blood, bone marrow or peripheral blood stem cell (hematopoietic stem cell) transplantation, attack of the host by the graft can be reduced, inhibited or eliminated by preconditioning the donor marrow by using the pretreatment methods disclosed herein in order to reduce the immunogenicity of the graft against the recipient. As described elsewhere herein, a donor hematopoietic stem and progenitor cell source can be pretreated with Tregs from any source, preferably with recipient Tregs in vitro prior to the transplantation of the donor marrow into the recipient. In a preferred embodiment, the donor marrow is first exposed to recipient tissue or cells and then treated with Tregs. Although not wishing to be bound to any particular theory, it is believed that the initial contact of the donor hematopoietic stein and progenitor cell source with recipient tissue or cells function to activate the T cells in the donor marrow. Treatment of the donor marrow with the Tregs induces hyporesponsiveness or prevents restimulation of T cells to subsequent antigenic stimulation, thereby reducing, inhibiting or eliminating an adverse affect induced by the donor marrow on the recipient.

In an embodiment of the present invention, a transplant recipient suffering from graft versus host disease or graft rejection may be treated by administering Tregs to the recipient to reduce, inhibit or eliminate the severity thereof from the graft versus host disease where the Tregs are administered in an amount effective to reduce or eliminate graft versus host disease.

In this embodiment of the invention, preferably, the recipient's Tregs may be obtained from the recipient prior to the transplantation and may be stored and/or expanded in culture to provide a reserve of Tregs in sufficient amounts for treating an ongoing graft versus host reaction. However, as discussed elsewhere herein, Tregs can be obtained from any source, for example, from the tissue donor, the transplant recipient or an otherwise unrelated source (a different individual or species altogether), Advantages of Using Tregs Based upon the disclosure herein, it is envisioned that the Tregs of the present invention can be used in conjunction with current modes, for example the use of immunosuppressive drug therapy, for the treatment of host rejection to the donor tissue or graft versus host disease. An advantage of using Tregs in conjunction with immunosuppressive drugs in transplantation is that by using the methods of the present invention to ameliorate the severity of the immune response in a transplant recipient, the amount of immunosuppressive drug therapy used and/or the frequency of administration of immunosuppressive drug therapy can be reduced. A benefit of reducing the use of immunosuppressive drug therapy is the alleviation of general immune suppression and unwanted side effects associated with immunosuppressive drug therapy.

It is also contemplated that the cells of the present invention may be administered into a recipient as a "one-time" therapy for the prevention or treatment of host rejection of donor tissue or graft versus host disease. A one-time administration of Tregs into the recipient of the transplant eliminates the need for chronic immunosuppressive drug therapy. However, if desired, multiple administrations of Tregs may also be employed.

The invention described herein also encompasses a method of preventing or treating transplant rejection and/or graft versus host disease by administering Tregs in a prophylactic or therapeutically effective amount for the prevention, treatment or amelioration of host rejection of the transplant and/or graft versus host disease. Based upon the present disclosure, a therapeutic effective amount of Tregs is an amount that inhibits or decreases the number of activated T cells, when compared with the number of activated T cells in the absence of the administration of Tregs. In the situation of host rejection of the transplant, an effective amount of Tregs is an amount that inhibits or decreases the number of activated T cells in the recipient of the transplant when compared with the number of activated T cells in the recipient prior to administration of the Tregs. In the case of graft versus host disease, an effective amount of Tregs is an amount that inhibits or decreases the number of activated T cells present in the transplant.

An effective amount of Tregs can be determined by comparing the number of activated T cells in a recipient or in a transplant prior to the administration of Tregs thereto, with the number of activated T cells present in the recipient or transplant following the administration of Tregs thereto. A decrease, or the absence of an increase, in the number of activated T cells in the recipient of the transplant or in the transplant itself that is associated with the administration of Tregs thereto, indicates that the number of Tregs administered is a therapeutic effective amount of Tregs.

The invention also includes methods of using Tregs of the present invention in conjunction with current mode, for example the use of immunosuppressive drug therapy, for the treatment of host rejection to the donor tissue or graft versus host disease. An advantage of using Tregs in conjunction with immunosuppressive drugs in transplantation is that by using the methods of the present invention to ameliorate the severity of the immune response following transplantation, the amount of immunosuppressive drug therapy used and/or the frequency of administration of immunosuppressive drug therapy can be reduced. A benefit of reducing the use of immunosuppressive drug therapy is the alleviation of general immune suppression and unwanted side effects associated with immunosuppressive drug therapy.

It should be understood that the methods described herein may be carried out in a number of ways and with various modifications and permutations thereof that are well known in the art. It may also be appreciated that any theories set forth as to modes of action or interactions between cell types should not be construed as limiting this invention in any manner, but are presented such that the methods of the invention can be more fully understood.

The following examples further illustrate aspects of the present invention. However, they are in no way a limitation of the teachings or disclosure of the present invention as set forth herein.

These methods described herein are by no means all-inclusive, and further methods to suit the specific application will be apparent to the ordinary skilled artisan. Moreover, the effective amount of the compositions can be further approximated through analogy to compounds known to exert the desired effect.

EXAMPLES

The invention is now described with reference to the following Examples. These Examples are provided for the purpose of illustration only, and the invention is not limited to these Examples, but rather encompasses all variations which are evident as a result of the teachings provided herein.

The experiments disclosed herein were conducted to develop and optimize approaches for the conversion and large-scale expansion of human $CD4^+25^+$ T cells from $CD4^+$ or $CD4^+25^-$ T cells, inducible Tregs (iTregs), for clinical trials including but not limited to prevent graft-versus-host disease (GVHD) after allogeneic transplant. The results disclosed herein demonstrate that iTregs can be generated using a combinatorial approach using tryptophan depletion/catabolites or a demethylating agent to initiate the iTreg conversion process, an mTOR inhibitor (e.g., rapa) to favor Treg conversion and outgrowth, and the later addition of a demethylating agent or a histone deacetylation inhibitor (HDACi) for imprinting iTregs after conversion.

Example 1

Expansion of $CD4^+25^+$Tregs

Figure 1B:
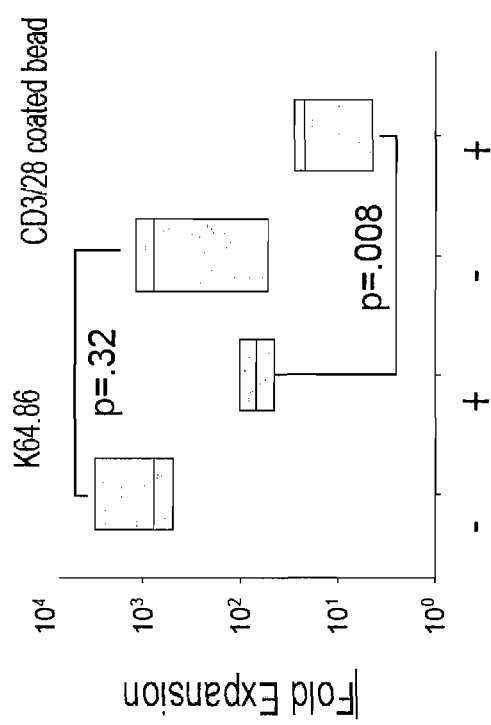

It has been previously shown that using research-grade beads for extensive negative selection followed by positive selection for $CD4^+25^+$ Tregs, and expanding the Tregs with anti-CD3/28 microbeads+IL-2 failed to generate uniformly suppressive cells. In addition, isolation of $CD4^+127$lo cells (CD127lo cells are approximately 10% of $CD4^+$ T cells) followed by anti-CD3/28 microbead/IL2 expansion did not permit uniform suppression (FIG. 1B). Although anti-CD3 mAb loaded K562 cells modified to express an FcR (CD64) and CD86 (KT64/86) was superior to anti-CD3/28 beads for expanding cells, a high level of suppression was not uniformly seen with either approach (FIG. 1B).

Adding rapa, which is an mTOR inhibitor, (labeled as +) reduced mean expansion rates by 30-fold with beads resulting in≤10-fold mean expansion rates by day 14. Rapa added to KT64/86 driven cultures (FIG. 1A) reduced mean expansion by 10-fold and improved suppression, although in some instances suppression was modest at high ratios (1:4) of Tregs to PBMNCs. The addition of TGFβ (10 ng/ml) to the cells did not increase suppression.

Since approximately 1-2% of $CD4^+$ T cells are CD25bright natural Tregs (nTregs) and incubation of these cells with rapa reduces their expansion, it is believed that at best, incubating nTregs with rapa is inefficient and at worst, the variability in suppressor cell potency has precluded clinical trials of ex vivo expanded peripheral blood Tregs to date. The next set of experiments were designed to convert $CD4^+$ T cells into inducible Tregs (iTregs) in order to utilize the 98-99% of $CD4^+$ T cells that are discarded when isolating $CD4^+$ T cells that are CD25bright nTregs. Without wishing to be bound by any particular theory, it is believed that converting $CD4^+$ T cells into iTregs also reduce the likelihood that non-Treg contaminants would result in loss of suppression.

Example 2

Figure 2:
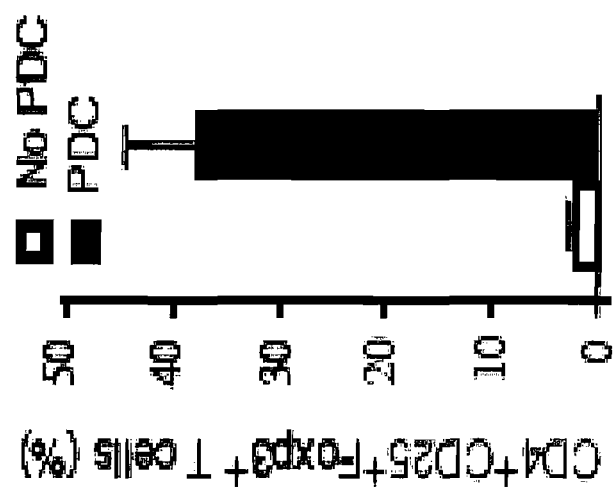
FIG. 2 is a chart demonstrating that culturing $CD4^+25^-$ T cells with allogeneic TLR9 activated allogeneic plasmacytoid dendritic cells (pDCs) leads to the generation of iTregs, $CD4^+25^+FoxP3^+$ suppressor cells.
Figure 3A:
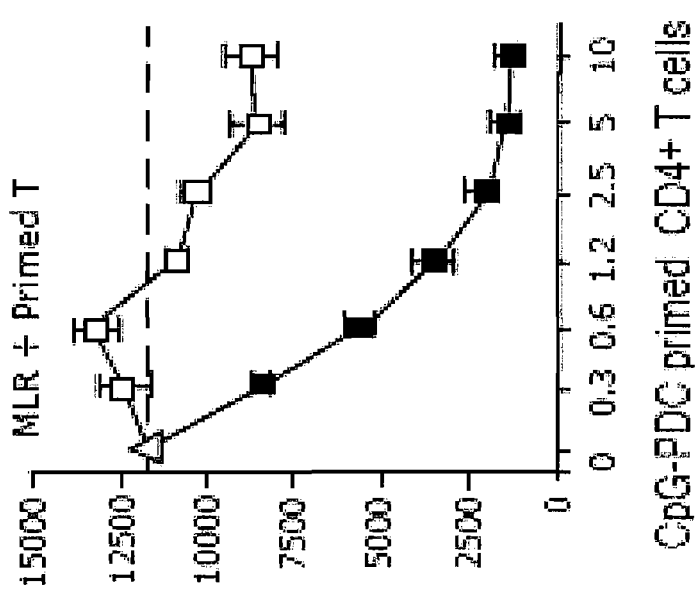
FIGS. 3A-3C, is a series of charts demonstrating that iTregs are immunosuppressive.
Figure 3B:
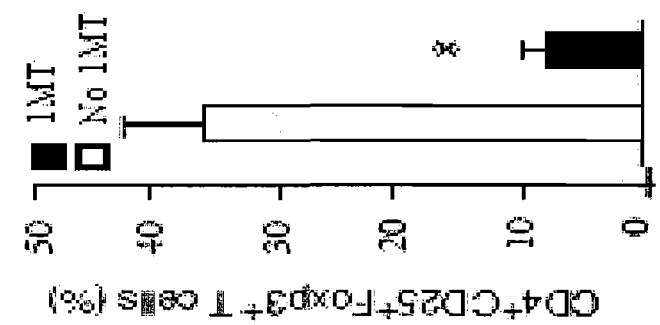
Figure 3C:
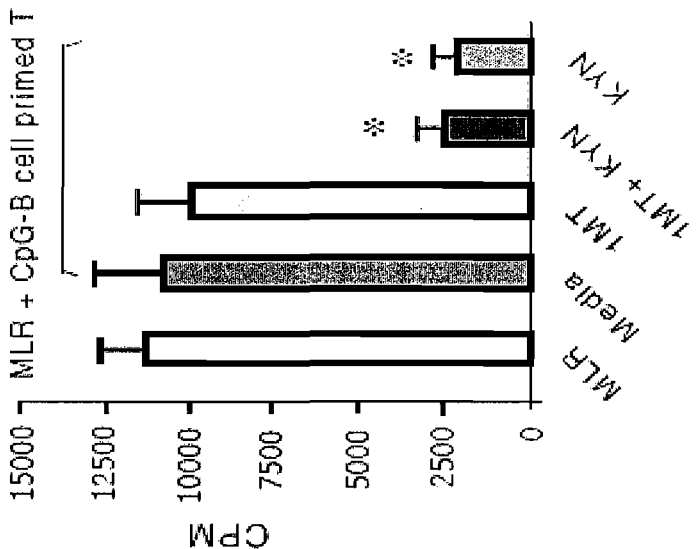

Culturing $CD4^+25^-$ T Cells and iTreg Generation $CD4^+25^-$ T cells, when cultured with allogeneic TLR9 activated allogeneic plasmacytoid dendritic cells (pDCs), but not B-cells, lead to the generation of iTregs, $CD4^+25^+FoxP3^+$ suppressor cells (FIG. 2). It was also observed that iTregs (closed), but not T cells primed to TLR activated B cells (open squares), were potently suppressive of a naïve MLR culture (x-axis are x 104; MLR used 105 naïve T cells; FIG. 3). It was observed that iTreg generation was dependent upon the enzyme indoleamine 2,3-dioxygenase (IDO) since IDO inhibition by 1-methyl-trypt (1MT) prevented conversion (FIG. 3B). Since IDO catabolizes tryptophan into kynurenines (KYN), it is believed that iTregs can be generated in B cell cultures using KYN. As shown in FIG. 3C, KYN resulted in potent MLR suppression that was not blocked by the addition of 1MT (KYN is downstream from IDO).

While these data provide proof-of-principle that KYN supports iTreg generation, the number of output iTregs equaled the input $CD4^+25^-$ T cells during MLR culture, To optimize iTreg conversion and expansion, experiments were designed to switch from the culture system to using a bead or cell based artificial APCs system and to compare the level of iTreg generation when $CD4^+25^-$ T cells were exposured to low levels of trypt/KYN or decitibine. To ensure naïve T cell conversion, rather than nTreg or T effector cell expansion, $CD4^+25^-45RA^+$ T cells were used.

For initial studies, to ensure inducible Treg (iTreg) conversion was being examined and not natural Treg (nTreg) expansion, CD4+25−45RA+ T cells are isolated from ficolled buffy coat cells by negative selection (CD8, CD11b, CD16, CD19, CD36, CD56 CD25) followed by CD45RA positive selection using beads. Cells are cultured in X-Vivo-15 or trypt-free media, as indicated, along with human ABneg serum (10%) and L-glutamine. rIL-2 (300 U/ml: Chiron) is added on day 2 and with re-feeds.

In order to assay for the presence of non-Tregs and nTregs, multi-color phenotyping can be employed pre- and post-isolation and on days 7, 10, 14, 21 for both non-Tregs and nTregs (CD4/25/127lo/FoxP3) for co-expression of adhesion molecules (e.g., CD62L; LFA-1), chemokine receptors (e.g., CCR 4-9; CXCR3), and cytokines (IL2, IL17, TNFa, IL10), Phosphorylated-Stat5 and p-Akt can be analyzed at 15' post-stimulation with PMA/ionomycin.

Figure 4:
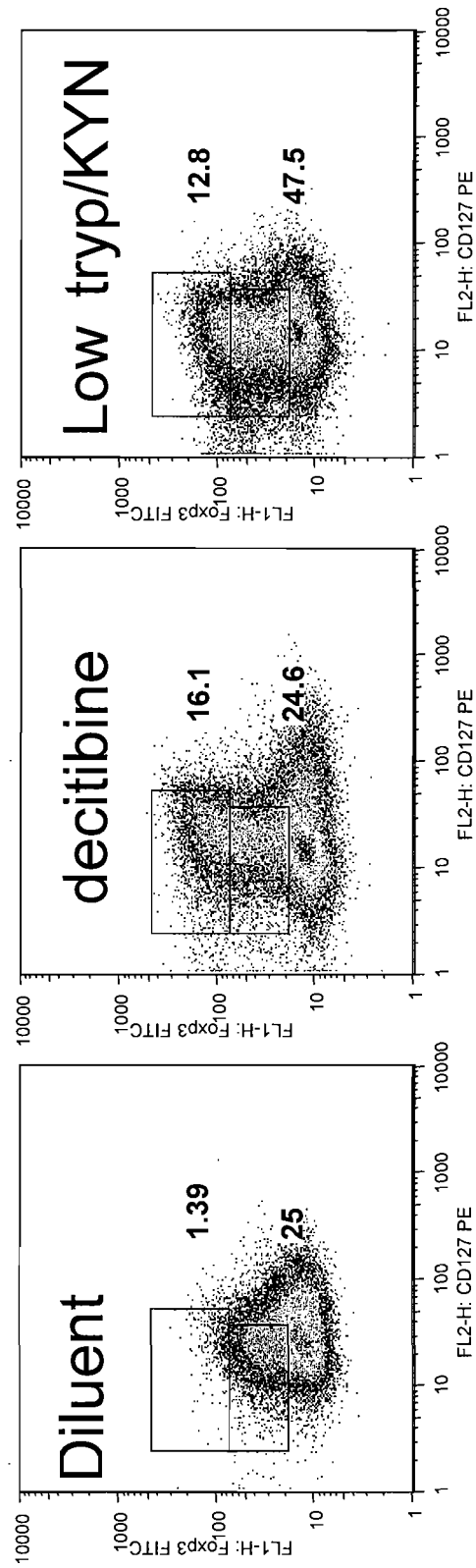
FIG. 4 is a series of charts summarizing the results of culturing $CD4^+CD25^-$ cells in diluent, decitibine, or tyrp/KYN. Diluent cultured cells expanded about 30-fold, decibine about 11 fold and low tryp/KYN about 5-fold; CD4+CD127loFoxP3hi cells were 1%, 16%, and 13%, respectively. FoxP3 levels relate to suppressor potency and stability. iTreg suppression of CD8+ T cell proliferation (1:16 ratio), assessed by quantifying CFSE dye-dilution, was 18%, 41% and 76%, respectively, indicating that FoxP3int cells present in the low trypt/KYN group were contributing to suppressor cell potency.

To simulate IDO effects, cells were cultured in low tryp+ KYN using KYN at 10 μM+trypt at 1 μM until day 7 then 5 μM trypt beyond day 7 to support expansion after iTreg "imprinting" has occurred. Decitibine was added at 1-5 μM (final) to day 3 cultures. Cultures were expanded with anti-CD3/28 mAb-loaded, irradiated KT32 (FcR+) cells, Anti-CD3/28 beads (3 beads:1 cell) or 100 Gy irradiated, anti-CD3 (OKT3) loaded KT64/86 cells (1 KT cell:2 CD4+25− T cells) are added on day 0. Cell density is maintained at 0.2-2×10⁶/ml by 50% vol/vol re-feeds, By 10 days, diluent cultured cells expanded about 30-fold, decibine about 11 fold and low tryp/KYN about 5-fold; CD4+CD127loFoxP3hi cells were 1%, 16%, and 13%, respectively (FIG. 4; upper, FoxP3hi; lower box, FoxP3int,lo). FoxP3 levels are related to suppressor potency and stability (Wan et al., 2007, Nature 445:766-70; Pillai et al., 2007, Clin Immunol 123:18-29; Williams et al., 2007, Nat Immunol 8:277-84). iTreg suppression of CD8+ T cell proliferation (1:16 ratio), assessed by quantifying CFSE dye-dilution, was 18%, 41% and 76%, respectively, suggesting that FoxP3int cells present in the low trypt/KYN group were contributing to suppressor cell potency. Taken together, these data indicate that large iTreg numbers could be generated without discarding 98-99% of CD4+ T cells needed to obtain CD4+25br cells and with expansion by day 10. In studies using umbilical cord blood (UCB) nTregs, day 11 cultures re-stimulated with KT cells expanded an additional 20-fold compared to no re-stimulation. These data indicate that iTregs can be generated in high numbers and suggest a strategy for maximizing iTreg expansion.

Example 3 iTreg Generation Using Histone Acetylation Followed By Demethylation

Recent studies have analyzed HDACi (suberoylanilide hydroxamic acid: SAHA; trichostatin A: TSA). SAHA and TSA target class I and II HDACs at μM and nM amounts, respectively (Dokmanovic, et al., 2007, Mol Cancer Res 5:981-9; Dangond et al., 1998, Biochem Biophys Res Commun 247:833-7). HDAC7 is affected by vorinostat and HDAC9 by TSA; both class IIa HDACs have been linked to FoxP3 regulation (Tao et al., 2007, Nat Med 13:1299-307; Dokmanovic et al., 2007, Mol Cancer Ther 6:2525-34). It has been observed that SAHA at 100 μM on day 0 was toxic, whereas SAHA at 300 nM on day 3 did not inhibit T cell expansion but also did not result in iTregs.

Figure 5A:
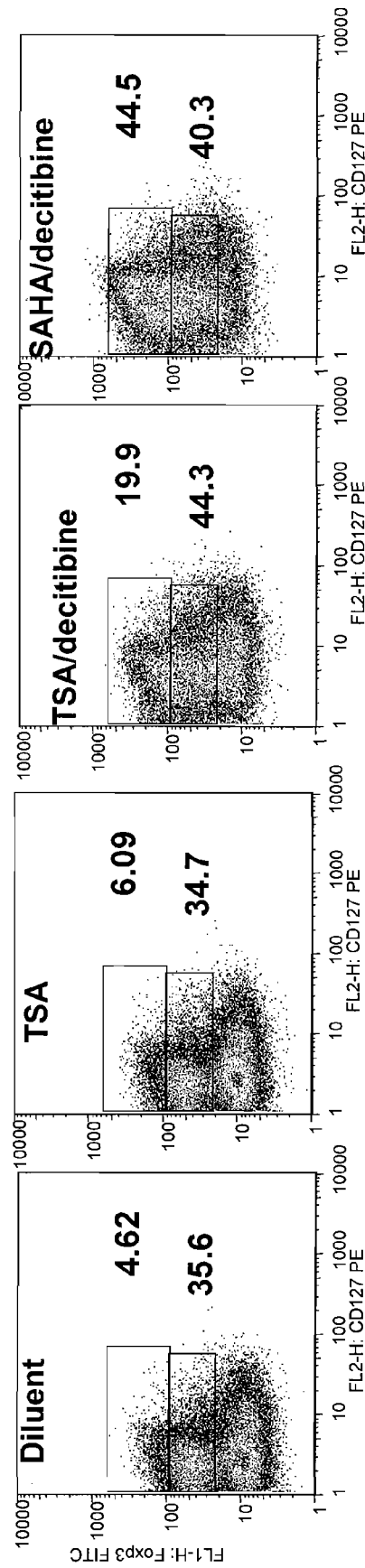
FIGS. 5A-5F, is a series of charts summarizing the results of culturing $CD4^+CD25^-$ cells in diluent, a demethylating agent, an HDACi, or a combination of a demethylating agent and an HDACi.

While HDACi is insufficient to result in iTregs in vitro (Tao et al., 2007, Nat Med 13:1299-307), it is believed that HDACi would be effective when used with decitibine, due to the known increase in histone methylation and deacetylation in Tregs and potential benefits of epigenetic modification on FoxP3 and Treg stability. Neither raps, TGFb (10 ng/ml), SAHA (300 nM) (not shown) nor TSA (100 nM) (FIG. 5) induced CD4+127loFoxP3hi cells by day 10. It was observed in cultures with day 3 SAHA or TSA, decitibine added on day 7 markedly increased CD4+127loFoxP3hi cells by day 10 from 4.6% (diluent) to 44.5% (SAHA/decitibine), indicating that histone acetylation followed by demethylation was advantageous for iTreg generation (FIG. 5A). Day 10 expansions were: diluent (20-fold), TSA (15-fold), TSA/decibine (6-fold), and SAHA/decitibine (7-fold). Although there was a decrement in total expansion rates between days 7-10 with decitibine, these cells were observed to recover and undergo vigorous growth. Based upon the percent FoxP3hi and FoxP3int cells in the SAHA/decitibine group, it is believed that suppression potency will exceed that observed with low tryp/KYN cultures in FIG. 4.

In the same experiment, bead expanded cultures revealed the following for CD4+127loFoxP3hi vs FoxP3int/lo: diluent (1.7, 21.8%); TSA (1.6%, 15.4%); TSA/decitibine (8.5%, 43.5%); SAHA/decitibine (7,9%; 41.1%). Despite the high iTreg levels, day 10 expansion was already 20-fold for TSA/ decibine and 23-fold for SAHA/decitibine.

Figure 5B:
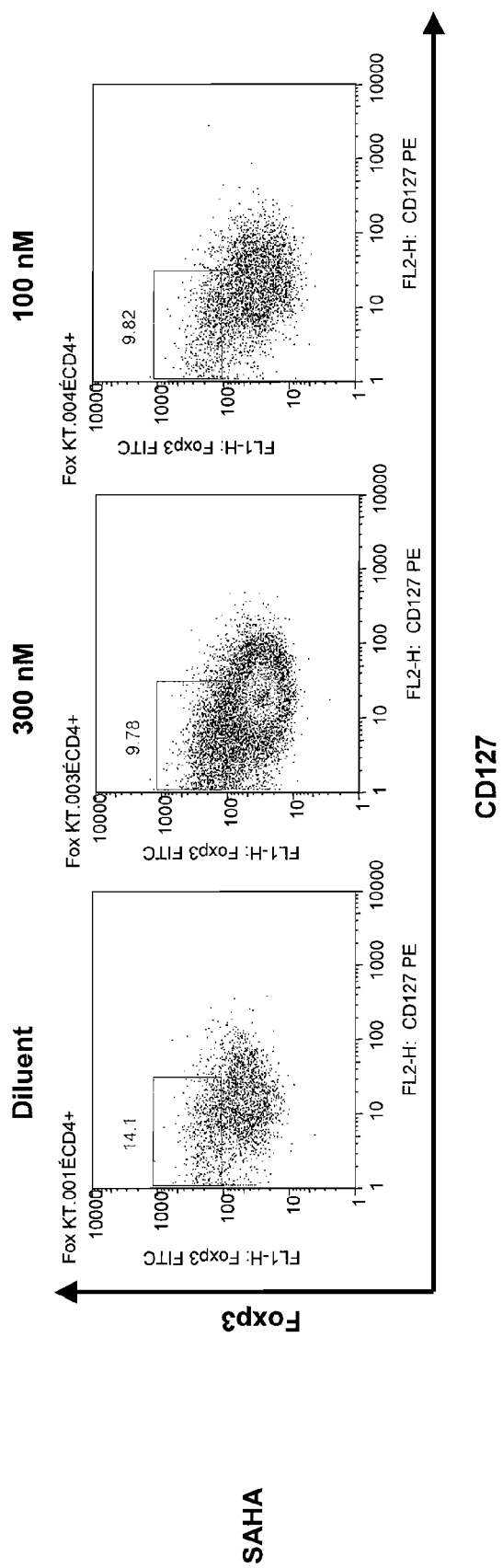
Figure 5C:
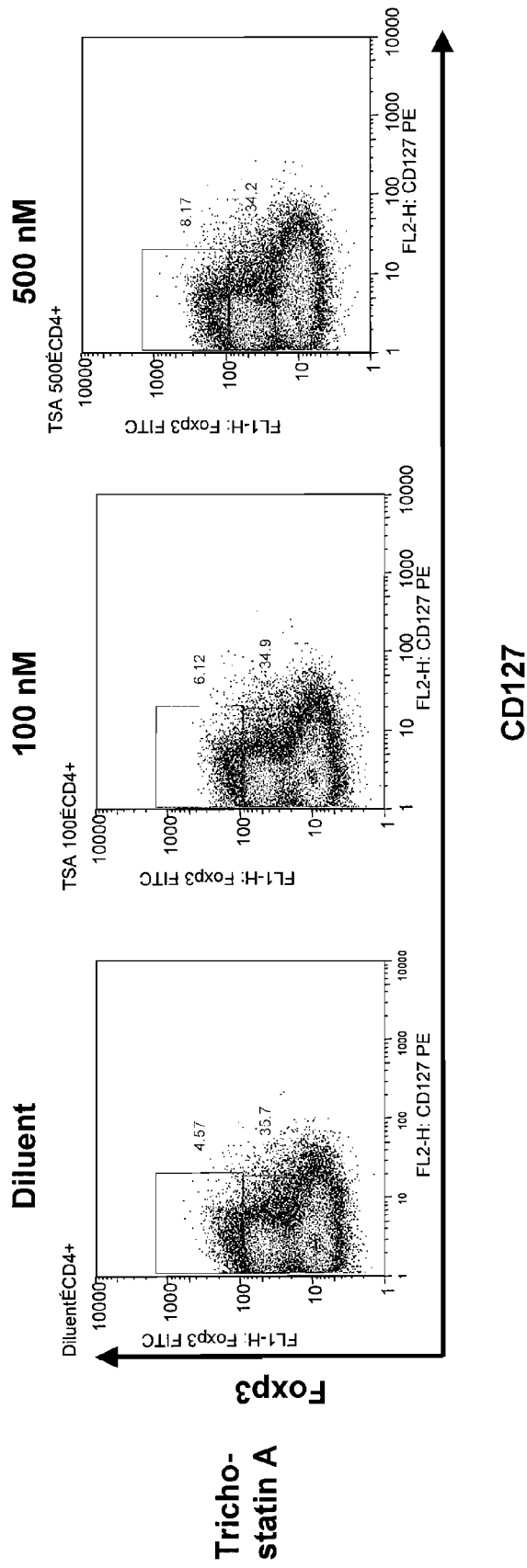

The next set of experiments were designed to compare the effects of a HDACi in a bead- or cell-based artificial antigen-presenting cell system (KT32) for generating iTregs (FIGS. 5B and 5C). Purified human naïve T cells (CD4+, CD25−, CD45RA+) were stimulated with KT32 (K562 engineered to express human CD32) loaded with anti-CD3 and CD28 antibodies. The cells were cultured for 3 days and SAHA added a single time at the indicated concentrations, and analyzed 7 days later (day 10) for Foxp3 expression (FIG. 5B). Purified human naïve T cells (CD4+, CD25−, CD45RA+) were stimulated with KT32 (K562 engineered to express human CD32) loaded with anti-CD3 and CD28 antibodies. The cells were cultured for 3 days and Trichostatin A added a single time at the indicated concentrations, and analyzed 7 days later (day 10) for Foxp3 expression.

Figure 5D:
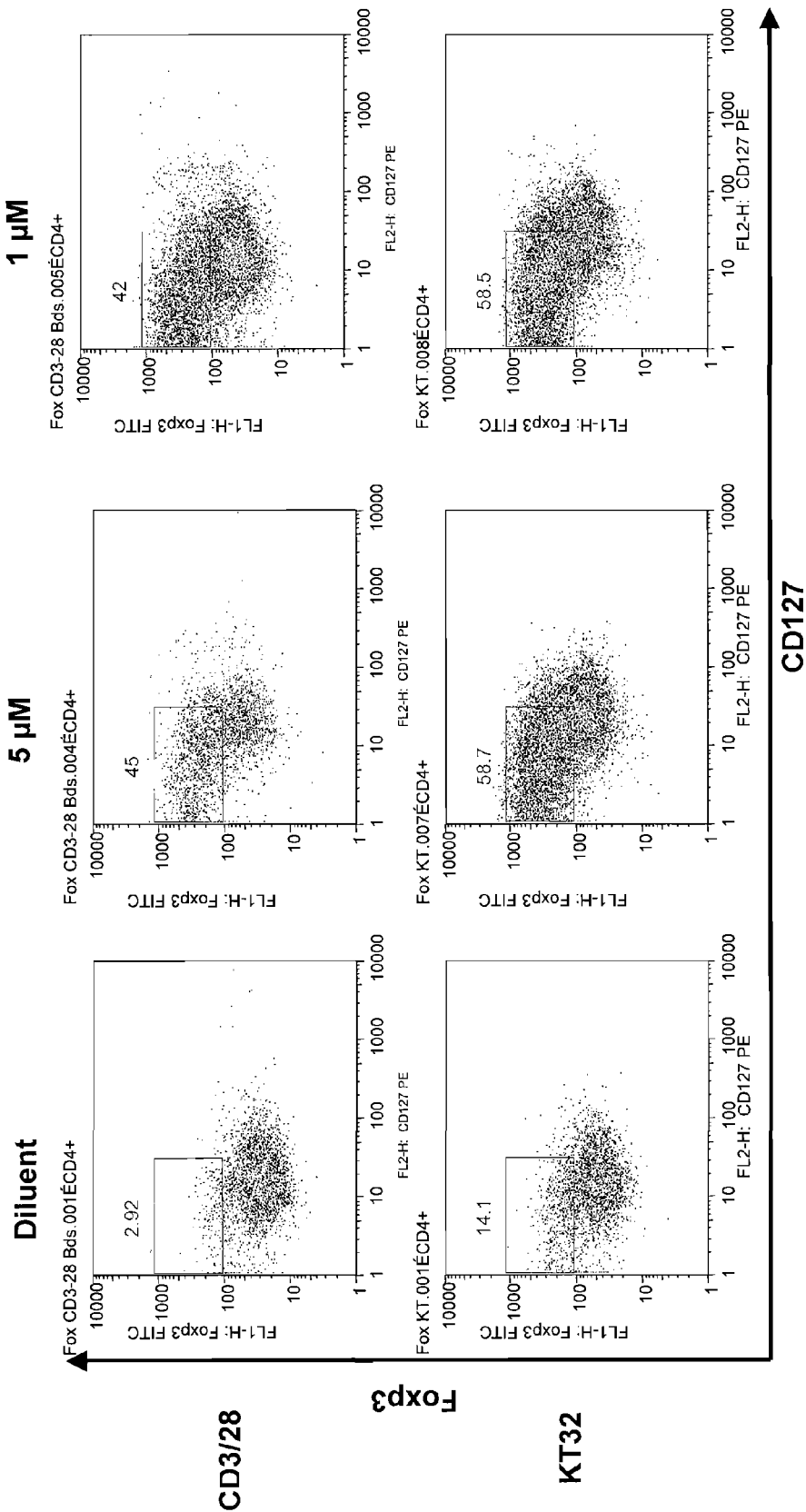
Figure 5E:
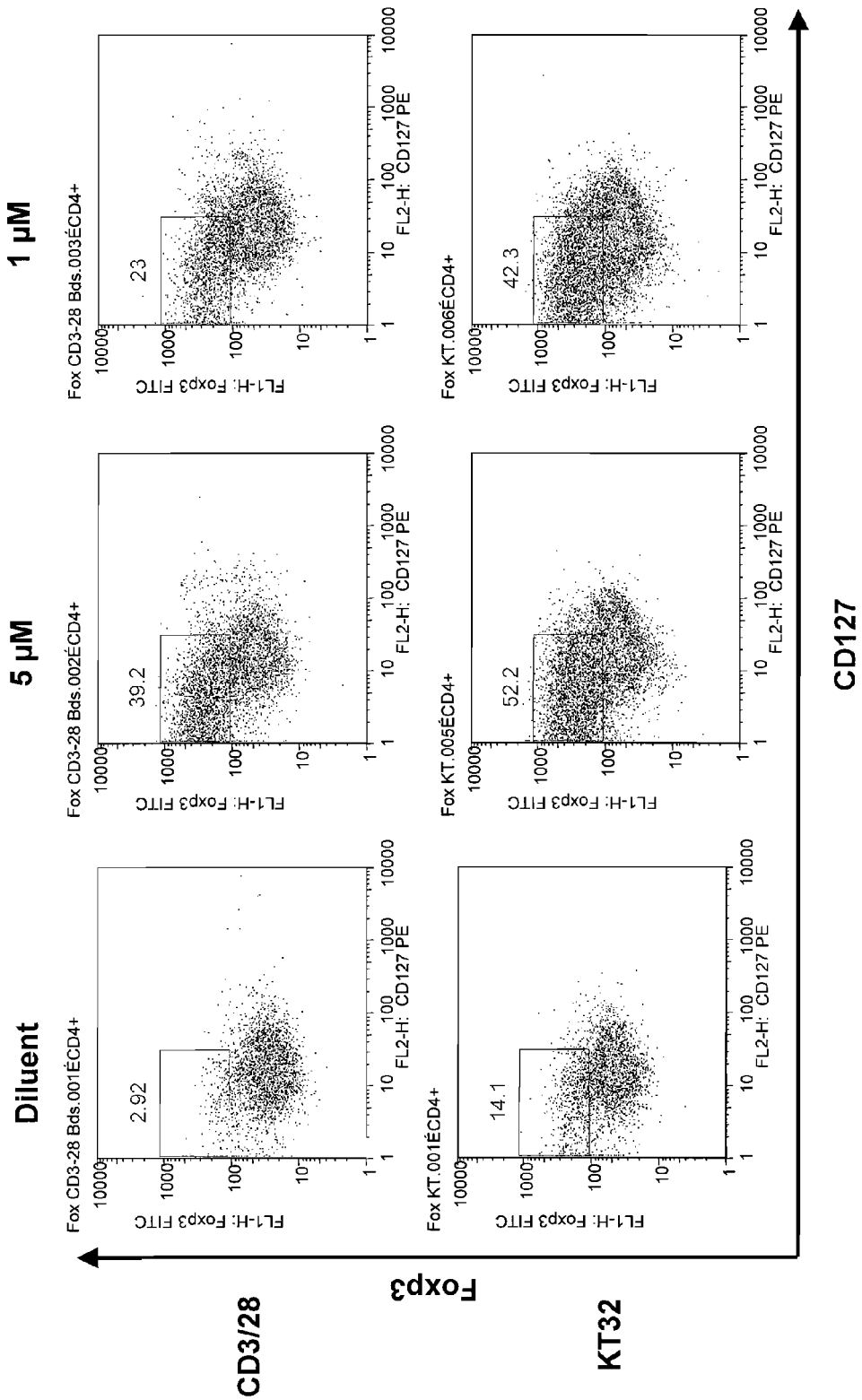

The next set of experiments were designed to compare the effects of a demethylating agent in a bead- or cell-based artificial antigen-presenting cell system (KT32) for generating iTregs (FIGS. 5D and 5E). Purified human naïve T cells (CD4+, CD25−, CD45RA+) were stimulated with clinical grade anti-CD3/28 beads or with KT32 (K562 engineered to express human CD32) loaded with anti-CD3 and CD28 antibodies. The cells were cultured for 3 days and Decitibine added a single time at the indicated concentrations, and analyzed 7 days later (day 10) for Foxp3 expression (FIG. 5D). Purified human naïve T cells (CD4+, CD25−, CD45RA+) were stimulated with clinical grade anti-CD3/28 beads or with KT32 (K562 engineered to express human CD32) loaded with anti-CD3 and CD28 antibodies. The cells were cultured for 3 days and 5-Azacytidine added a single time at the indicated concentrations, and analyzed 7 days later (day 10) for Foxp3 expression (FIG. 5E).

Figure 5F:
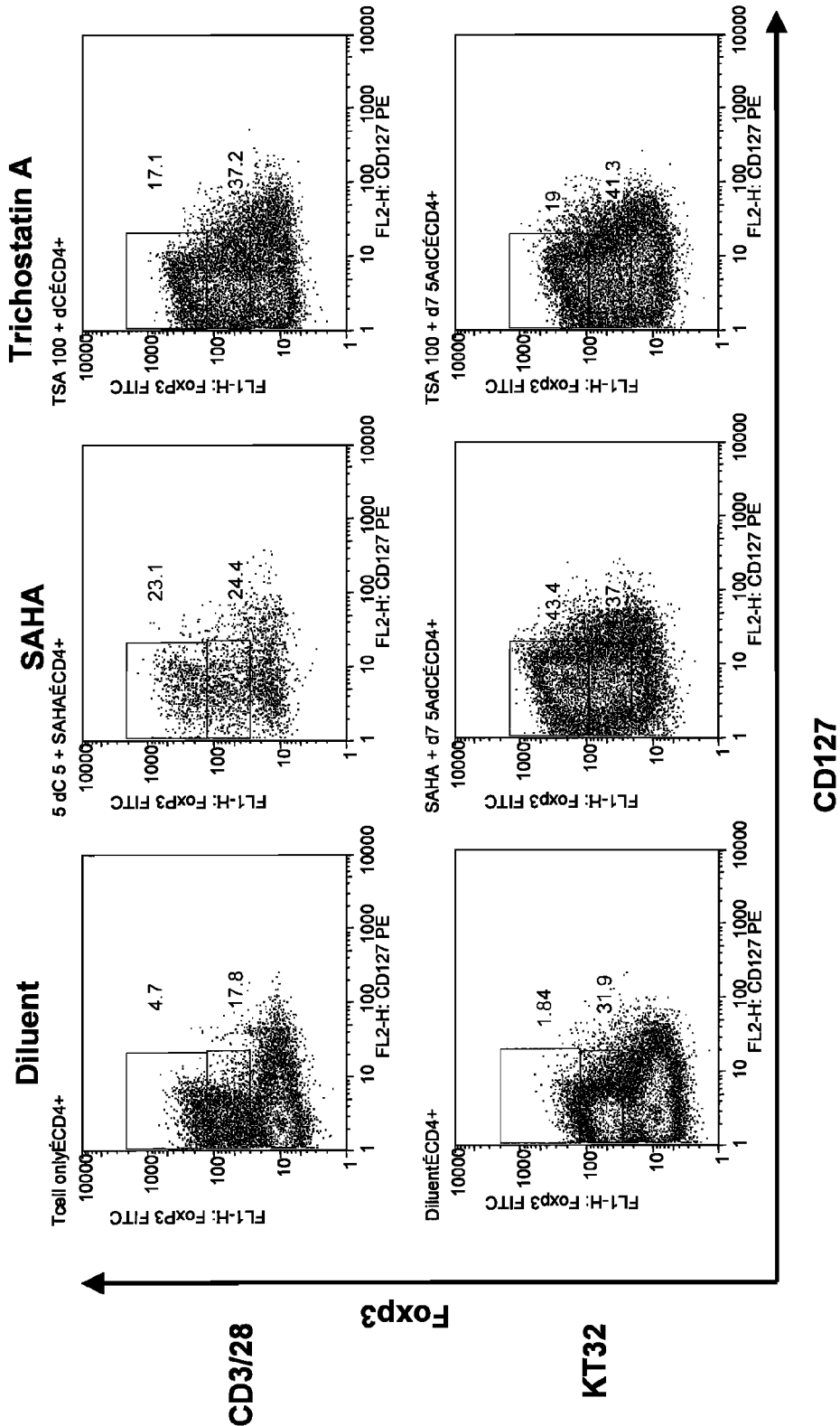

The next set of experiments were designed to compare the effects of the combination of an HDACi with a demethylating agent in a bead- and cell-based antigen-presenting cell system (FIG. 5F). Purified human naïve T cells (CD4+, CD25−, CD45RA+) were stimulated with clinical grade anti-CD3/28 beads or with KT32 (K562 engineered to express human CD32) loaded with anti-CD3 and CD28 antibodies. On day 3 of culture, the specified HDACi were added. On day 7, a single dose of Decitibine (1 µM) was added and cultures analyzed 3 days later (day 10) for Foxp3 expression.

Example 4 iTreg Generation and Monitoring

Methylation and histone deacetylation typically suppress gene transcription (Tao et al., 2007, Curr Opin Immunol 19:589-95). In comparison to non-Tregs, natural Tregs (nTregs) are hypomethylated and it has been observed that complete demethylation and histone modifications occur in the FoxP3 locus of nTregs (Floess et al., 2007, PLoS Biol 5:e38; Baron et al., 2007, Eur J Immunol 37:2378-89). Consistent with importance of epigenetic modification for iTreg stability, re-stimulation of TGFb-generated iTregs in the absence of TGFb results in loss of FoxP3 and suppression (Floess et al., 2007, PLoS Biol 5:e38). In rodents, a histone deacetylation inhibitor (HDACi) supported in vivo rodent iTreg generation in nTreg-depleted but not Treg-replete recipients (Tao et al., 2007, Nat Med 13:1299-307). It is reported that nTregs are less dependent than non-Tregs on the mTOR/Akt pathway. Rapa, an mTOR inhibitor, has been shown to suppress non-Tregs and favor iTreg conversion (Zeiser et al., 2008, Blood 111:453-62; Battaglia et al., 2005, Blood 105:4743-8; Coenen et al., 2006, Blood 107:1018-23; Haxhinasto et al., 2008, J Exp Med 205(3):565-74).

The following experiments were designed to determine the optimal approach for iTreg generation and expansion, to quantify iTreg potency and functional stability in vitro and in vivo, and to perform large-scale GMP-production of iTregs for clinical trial implementation.

The results presented herein demonstrate that iTregs can be generated in tryptophan (trypt) depletion conditions. In addition, the results demonstrate the use of a combinatorial approach to generate iTregs using trypt depletion/catabolites or a demethylating agent to initiate the iTreg conversion process, rapa to favor Treg conversion and outgrowth, and the later addition of a demethylating agent or HDACi for imprinting iTregs. Potency and suppressor function stability of the iTregs can be measured in vitro and in a xenogeneic GVHD model.

A matrix-type approach may be used for sequential and when desired, experiments are designed for combinatorial testing of optimal concentrations of single agents guided by assays described below.

Decitibine

Around 1-5 µM decitibine may be added day 3 vs days 3+7 (to further imprint cells). Hypomethylation is assessed using bisulfite sequencing (Baron et al., 2007, Eur J Immunol 37:2378-89; Issa et al., 2005, J Clin Oncol 23:3948-56) and comparisons made to days 7 & 21 between expanded nTregs and flow-sorted adult peripheral blood Tregs. H3 and H4 histone acetylation can be assessed under various conditions by Western blot and ELISA (O'Connor et al., 2006, J Clin Oncol 24:166-73; Garcia-Manero et al., 2008, Blood 111: 1060-6) to determine the extent to which iTreg protocols are associated with histone acetylation and HDACi alter this pattern. CHOP staining may be used as an indicator of the GCN2 kinase stress response (for trypt/KYN) (Sharma et al., 2007, J Clin Invest 117:2570-82), and p-serine473-Akt (for rap) (Crellin et al., 2007, Blood 109:2014-22) may be monitored at time points as above. Without wishing to be bound by any particular theory, an acceptable range for using a demethylating agent (e.g., 5-aza-2'-deoxycitidine (decitibine), 5-Azaeytidine) according to the invention is believed to be around 0.1 to 100 µM.

Trypt/KYN

A preferred approach to generate iTregs is to induce a stress response. For example addition of trypt at 1 µM for 7 days followed by more permissive growth conditions, trypt at 5 µM; trypt metabolites (3HK, 3HAA, QA, AA, L-KYN; Sigma) are added at 10 µM (final) on day 0 and with re-feeds. Without wishing to be bound by any particular theory, an acceptable range for using trypt or trypt metabolite according to the invention is around 1-100 µM.

SAHA

SAHA (Merck) may be added at ranges of 300-1000 nM on day 7 and with re-feeding in cultures initiated with decitibine or low trypt/KYN. Conversely, decitibine may be added on day 7 to SAHA initiated cultures (see FIG. 5). Without wishing to be bound by any particular theory, an acceptable range for using a HDACi according to the invention is around 10 nM to 1 µM for TSA, and around 50 nM to 5 µM for SAHA.

Rapa

Rapa (109 nM; Wyeth-Ayerst) may be added on 0 and with re-feeds along with decitibine, trypt/KYN or HDACi (day 3 or day 7). Alternatively, rapa may be added on day 7 and with re-feeds after initial iTreg imprinting has occurred to facilitate iTreg conversion and prevent non-Treg outgrowth, minimizing the impact of day 0 rapa on cell yield. Without wishing to be bound by any particular theory, an acceptable range for using Rapa according to the invention would be about 10-1000 nM Rapa (Wyeth).

Example 5

In Vivo Potency of Expanded iTregs

To quantify in vivo GVHD inhibitory capacity, C57BL/6-IL2Rgc/rag knockout mice were macrophage depleted using clodronate, sublethally irradiated, and given PBMNC (30× 106)±a suboptimal number (10×106) of anti-CD3/28 beads or irradiated, anti-CD3/28 mAb loaded KT cell line expanded UCB nTregs iv. While both nTreg sources significantly reduced GVHD lethality, nTregs generated with KT cells were superior to those with beads. Day 10 peripheral blood analysis indicated that KT vs. bead expanded Tregs were present in significantly higher numbers. Human CD4+ and CD8+ T cells present in the spleen at the time of death were reduced by nTregs, with the greatest effects observed using KT expanded nTregs. Human PBMNCs cause severe GVHD of the liver, lung and ileum (mean scores>3.0 on a 4 point scale), associated with human T cell infiltration into these organs (not shown). This model is useful to quantify in vivo potency of expanded iTregs vs nTregs cultured and to facilitate iTreg choice for trials.

In vitro potency of expanded iTregs vs nTregs may be assayed for suppression in MLR and anti-CD3 mAb driven, CD8+ CFSE T cell proliferation assays. Those approaches that are the most potent via in vitro assays while permitting at least a 10-fold expansion over $CD4^+25^-$ input number are assessed by dose titrations of iTregs vs nTregs using the above described xenogeneic GVHD model. iTregs and nTregs are mismatched for PBMNCs at HLA-A2 or HLA-B7 to permit HLA flow typing of peripheral blood on days 7-14 and tissue analysis along with survival, weight loss and GVHD scoring.

Stability of iTregs can be measured by assessing FoxP3. FoxP3 acts in a dose-dependent non-binary fashion to control suppressor function (Wan et al., 2007, Nature 445:766-70). A transient Treg phenotype has been described (Pillai et al., 2007, Clin Immunol 123:18-29). FoxP3 loss results in suppression loss (Williams et al., 2007, Nat Immunol 8:277-84). iTregs and nTregs may be phenotyped for TNFα, IFNγ, IL17 and receptors that induce Th17 cells (IL6R, IL23R, CCR4, CCR6, RORgt) and exposed to conditions for Th17 generation and expansion (anti-CD3/28 mAbs; IL-23, IL6, IL1b, TNFα, TGFβ1, and mAbs to IL4, IL12, and IFNγ (Weaver et al., 2006, Immunity 24:677-88; Nurieva et al., 2007, Nature 448:480-3; Yang et al., 2008, Immunity 28:29-39; Stockinger et al., 2007, Curr Opin Immunol 19:281-6; Veldhoen et al., 2006, Immunity 24:179-89; Korn et al., 2007, Nature 448: 484-7; Singh et al., 2008, J Immunol 180:214-21). Experiments are designed to analyze Tregs for Th17, Th1 and Th2 conversion along with FoxP3 expression in the xenogeneic GVHD model with HLA typing of PB and GVHD organs. If Th17 cells are seen, all trans-retinoic acid (ATRA), 0.1-1 μM (Schambach et al., 2007, Eur J Immunol 37:2396-9; Elias et al., 2008, Blood 111:1013-20; Benson, et al., 2007, J Exp Med 204:1765-74), may be added on day 0 or on day 7, to minimize its anti-proliferative effects and repeat potency and stability studies.

Example 6

Clinical Trial $CD4^+25^+$ natural Tregs (nTregs) have been shown to have the ability to prevent GVHD, donor bone marrow graft rejection, and in speeding immune recovery in GVHD-prone mice (Gregori et al., 2005, Curr Opin Hematol 12:451-6; Blazar et al., 2005, Biol Blood Marrow Transplant 11:46-9). Clinical testing adult peripheral blood (PB) Tregs has been hampered of by the low frequency and less distinct CD4/25br subset and availability of GMP reagents for rigorous Treg purification (June et al., 2006, Semin Immunol 18:78-88). Isolation and expansion protocols can result in suppression loss when about 5% non-Treg are present. Umbilicord blood Tregs exist at higher frequency, have a distinct CD4/25br subset readily purified using CD25 mAb-coated beads and can be expanded by about 200-1000 fold in <3 weeks using anti-CD3/28 mAb-coated beads+IL-2 (Porter et al., 2006, Transplantation 82:23-9; Godfrey et al., 2005, Blood 105:750-8).

It has been shown that $CD4^+25^-$ T-cells exposed to allogeneic TLR9 activated plasmacytoid dendritic cells (pDCs), but not B-cells, leads to the generation of iTregs (Moseman et al., 2004, J Immunol 173:4433-42), $CD4^+25^+FoxP3^+$ suppressor cells, a process dependent upon the enzyme indoleamine 2,3-dioxygenase (IDO) that catabolizes tryptophan. Adding 50 μM trypt catabolites (kynurenines: KYN) to allogeneic B-cell cultures generated potently suppressive iTregs. Because obtaining high numbers of non-malignant B-cells or pDCs from leukemia/lymphoma patients would be difficult, low trypt/KYN conditions in an artificial antigen-presenting cell expansion system was examined. In considering strategies for iTreg generation, experiments were designed to focus on molecular features preferentially associated with nTregs vs naïve or T effector cells. Compared to non-Tregs, nTregs have hypomethylated DNA and upon T cell receptor signaling, FoxP3 binding to CD25, GITR, CTLA4 increases histone acetylation (Chen, et al., 2006, J Biol Chem 281:36828-34). nTregs are in a state of hypomethylation and histone acetylation. In leukemias, tumor suppressor genes are inactivated by oncogenic transformation and demethylating agents (decitibine) and HDACi (SAHA, vorinostat) are used for treatment (O'Connor et al., 2006, J Clin Oncol 24:166-73; Garcia-Manero et al., 2008, Blood 111:1060-6; Issa et al., 2005, J Clin Oncol 23:3948-56; Issa et al., 2004, Blood 103: 1635-40).

Without wishing to be bound by any particular theory, the aforementioned agents are useful for large-scale iTreg generation. mTOR/Akt signaling is upregulated in myeloid leukemias and rapa is used for AML/MDS therapy (Yee et al., 2006, Clin Cancer Res 12:5165-73). Adding rapa to peripheral blood Treg cultures favors iTregs and nTregs due to higher dependency of non-Tregs on mTOR/p-Akt for proliferation and survival (Zeiser et al., 2008, Blood 111:453-62; Battaglia et al., 2005, Blood 105:4743-8; Coenen et al., 2006, Blood 107:1018-23; Haxhinasto et al., 2008, J Exp Med 205(3):565-74). The results presented herein demonstrate that combinatorial approaches of low trypt/KYN, decitbine, SAHA and rapa may be used for converting non-Tregs into Tregs.

Studies are performed to determine whether CD25+ T cells should be depleted (w/CD25 beads) and whether CD45RA positive selection is needed by comparing results of $CD4^+$, $CD4^+25^-$, $CD4^+45RA^+$ and $CD4^+25^-CD45RA^+$ input T cells using the preferred iTreg protocol. CD45Ra beads or anti-CD45Ra mAb may be used in conjunction with Miltenyi.

Expansion procedures include using a bead- or cell-based artificial antigen-presenting cell system (CD3/28 beads vs KT64/86 cells). T cells are cultured at 1×106/ml in the appropriate culture vessel and stimulated with IL-2 (300 U/ml) and anti-CD3/28 beads or OKT3-loaded, irradiated KT64/86 cells. Cultures are diluted 1:1 on day 3 with media/IL2 to maintain T cell:APC clusters. On day 7, cultures are split into larger vessels and re-plated to 0.5×106/ml thrice weekly.

The next set of experiments is a phase I dose escalation trial of peripherial blood nTregs. Patients with malignancy and HLA genotypic identical donors are subjects for the phase I trial. The trial is designed to include standard GVHD prophylaxis agents previously shown not to have a deleterious effect on Treg function in vitro. With the high numbers of iTregs generated from the combinational approach discussed herein, a 3rd infusion on day 28 can be readily incorporated into this platform.

Ultimately, the methods discussed herein are useful for manufacturing sufficient iTregs for about two to three infusions after cryopreservation after the completion of in vitro and in vivo potency and stability assays. Once the maximal tolerable dose is determined and in vivo activity is verified, it is anticipated that the next generation of clinical trials will eliminate calcineurin-inhibitors, steroids and other agents, as post transplant immunosuppression (eg. rapa, MMF).

Example 7

Restimulation of iTreg

Figure 6:
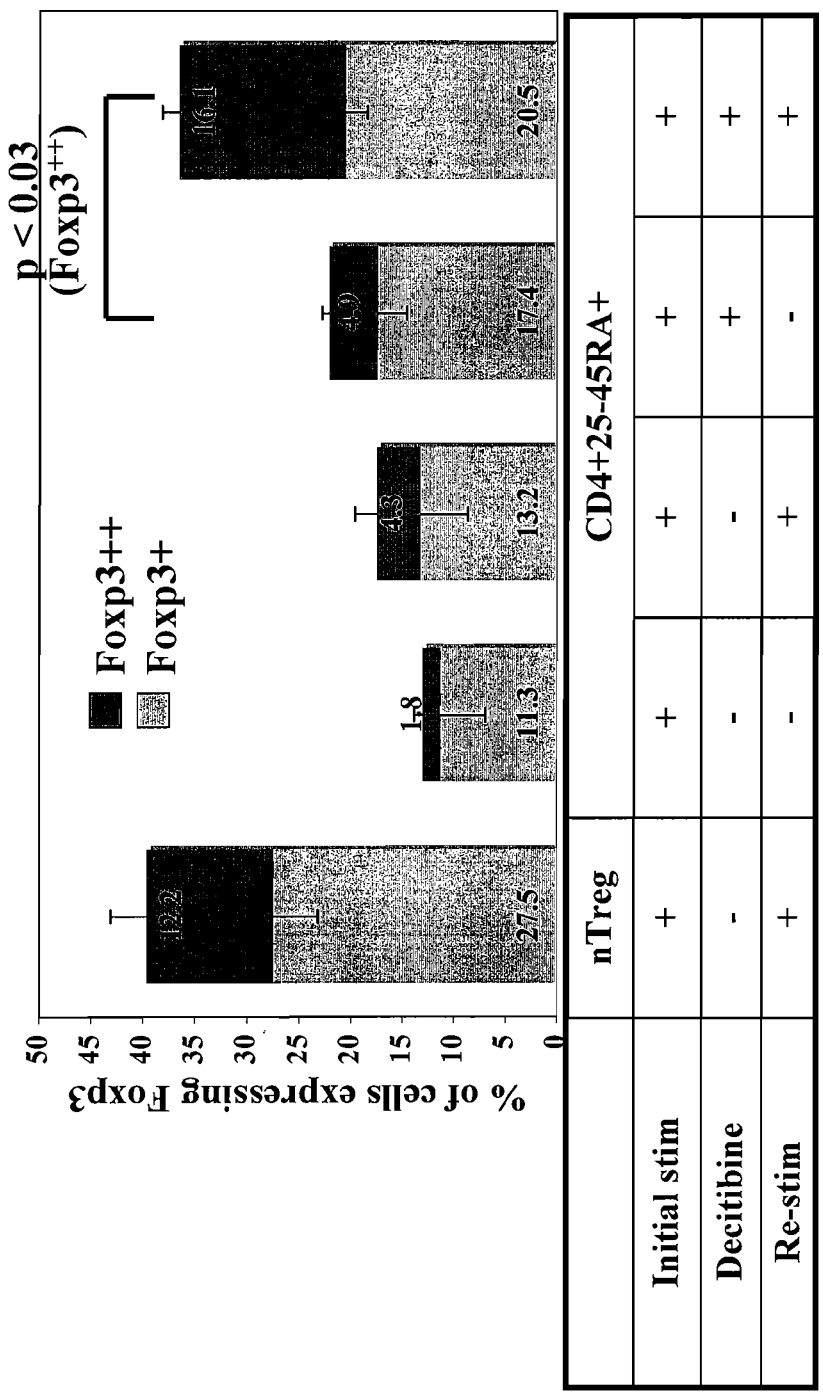
FIG. 6 is an image demonstrating that re-stimulation of iTreg on day 7 increases the percentage of Foxp3++ cells. nTreg ($CD4^+25^{++}$) and $CD4^+25^-45RA^+$ cells were purified from peripheral blood (PB) using magnetic beads and stimulated with anti-CD3 loaded KT64/86. Re-stimulation of CD4+25-CD45RA+ cells does not significantly effect Foxp3 levels, but the percentage of Foxp3++ are significantly increased in the presence of Decitibine.

The next set of experiments was designed to determine whether re-stimulation of iTreg increases the percentage of Foxp3++ cells. nTreg ($CD4^+25^{++}$) and $CD4^+25^-45RA^+$ cells were purified from peripheral blood (PB) using magnetic beads and the cells were stimulated with anti-CD3 loaded KT64/86 cells (K562 cells modified to express an Fc receptor CD64 and CD86). nTreg were cultured in the presence of IL-2 (300 U/ml) and Rapamycin (109 nM) while $CD4^+25^-$ cells were cultured with IL-2 alone, or were induced to become Treg by the addition of Decitibine (5 μM at day 7) and Raparnycin (109 nM at day 7). Portions of the $CD4^+25^-$ $45RA^+$ and Decitibine iTreg cultures were also re-stimulated on day 7 with anti-CD3 loaded KT64/86 cells. After a total of 14 days, cells were harvested and the expression of CD4, CD25, and Foxp3 was measured using flow cytometry. FIG. 6 summarizes the results in the context of percentage of CD4+ gated cells expressing low (Foxp3+) or high (Foxp3++) levels of Foxp3. It was observed that re-stimulation of CD4+25– CD45RA+ cells does not significantly effect Foxp3 levels.

However, the percentage of cells that were Foxp3++ was significantly increased in the Decitibine iTreg group following re-stimulation.

Figure 7A:
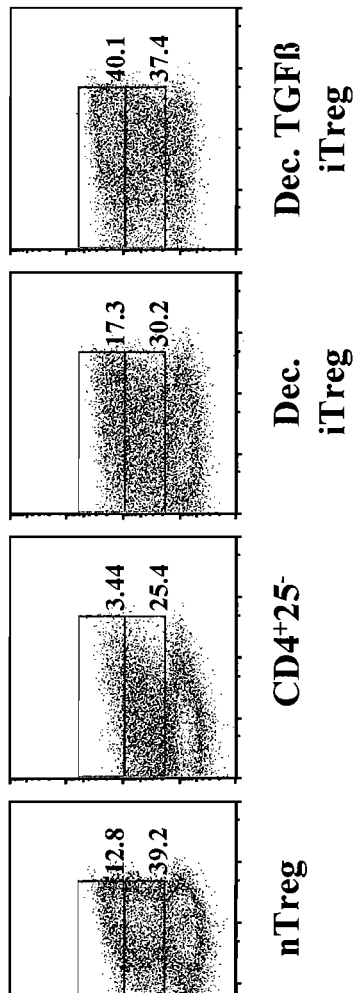
FIGS. 7A and 7B, is a series of images demonstrating that TGFβ synergizes with Decitibine to induce Foxp3 expression.
Figure 7B:
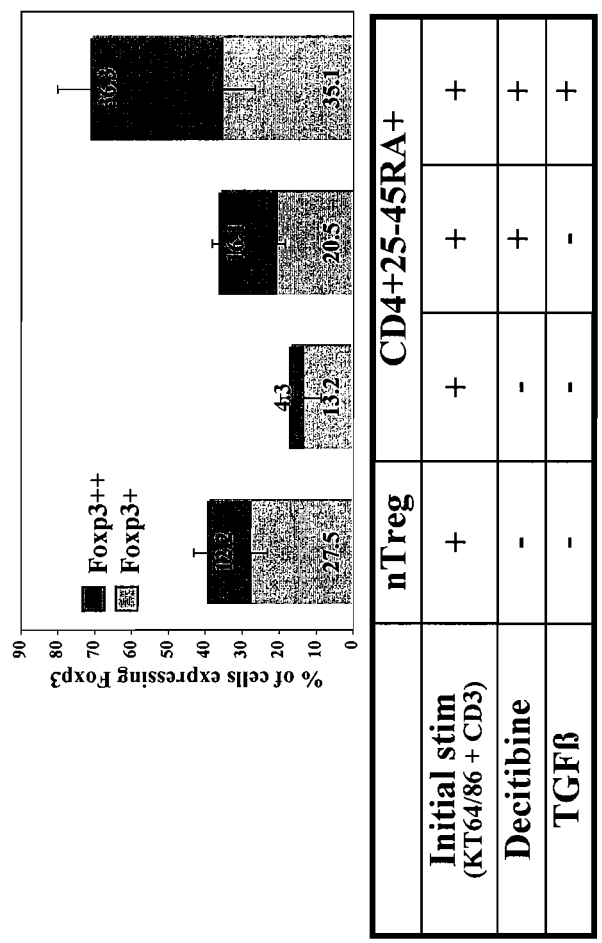

The next set of experiments was designed to determine whether TGFβ could synergize the effects of Decitibine to induce Foxp3 expression in the cells. Briefly, nTreg (CD4$^+$25$^{++}$) and CD4$^+$25$^-$45RA$^+$ cells were purified from peripheral blood using magnetic beads and stimulated with anti-CD3 loaded KT64/86 cells. nTreg were cultured in the presence of IL-2 (300 U/ml) and Rapamycin (109 nM) while CD4$^+$25$^-$ cells were cultured with IL-2 alone, or were induced to become Treg by the addition of Decitibine (5 μM at day 7) in the presence or absence of TGFβ (10 ng/ml, day 0). All samples were re-stimulated on day 7 with anti-CD3 loaded KT64/86 cells. After a total of 14 days, cells were harvested and expression of CD4, CD25, and Foxp3 was measured using flow cytometry. It was observed that while stimulation of CD4$^+$25$^-$45RA$^+$ cells and Decitibine treated CD4$^+$25$^-$45RA$^+$ cells with anti-CD3 loaded KT64/86 cells resulted in some Foxp3 expression, Foxp3 expression was significantly increased when CD4$^+$25$^-$45RA$^+$ cells were treatment with both Decitibine and TGFβ, especially the Foxp3++ cells (P≤0.01 and ≤0.002 for unmanipulated vs. cells treated with Decitibine or Decitibine/TGFβ, respectively). See FIG. 7.

Figure 8:
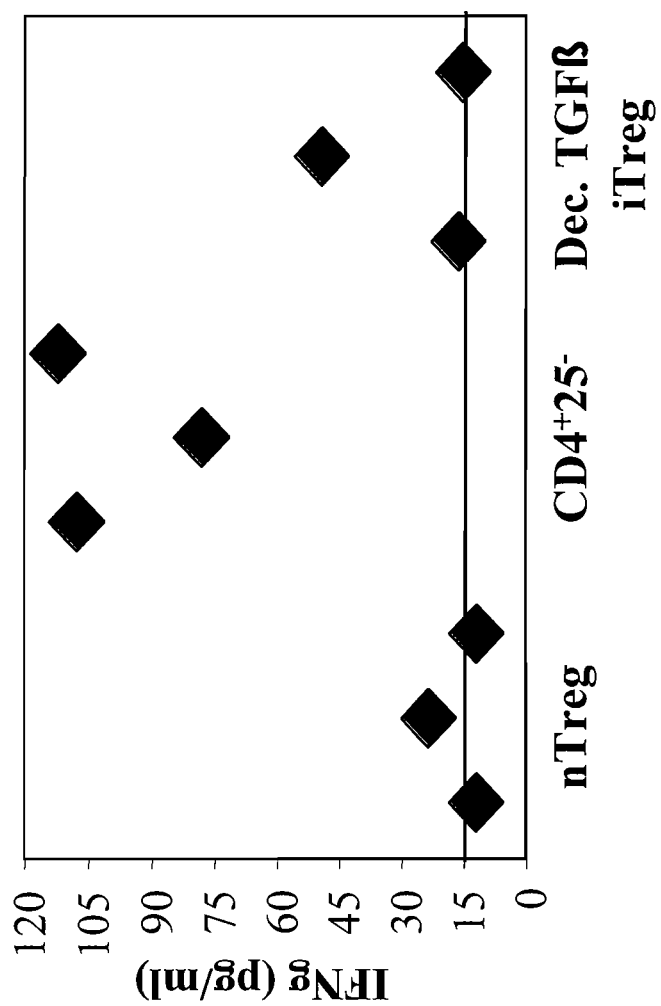
FIG. 8 is an image demonstrating that Tregs induced with Decitibine and TGFβ was observed to do not secrete IFNγ.

The next set of experiments was designed to determine whether Tregs induced with Decitibine and TGFβ secrete IFNγ. nTreg (CD4+25++) and CD4+25–45RA+ cells were purified from PB using magnetic beads and were stimulated as discussed elsewhere herein. After 12 days, cells were washed, resuspended in fresh media and incubated for an additional 2 days, after which the cells were removed by centrifugation and the supernatants assayed for IFNγ, FIG. 8 indicates that Tregs induced with Decitibine and TGFβ do not secrete IFNγ. The line at 15 pg/ml in FIG. 8 represents the sensitivity of the assay. Supernatants were also assayed for IL-17, but significant amounts of this cytokine were not detected (not shown).

Figure 9A:
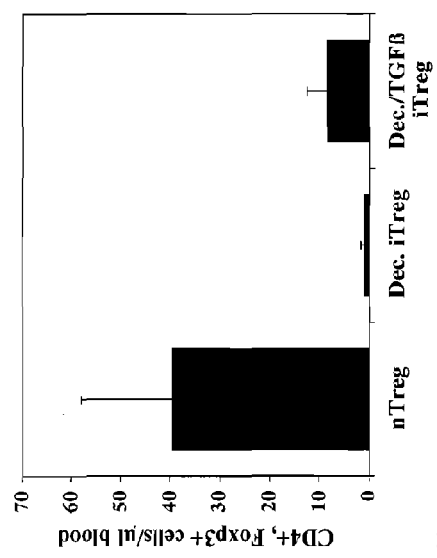
FIGS. 9A and 9B, is a series of images demonstrating that Decitibine and Decitibine/TGFβ induced Tregs decrease mortality in a xenogeneic model of GVHD.
Figure 9B:
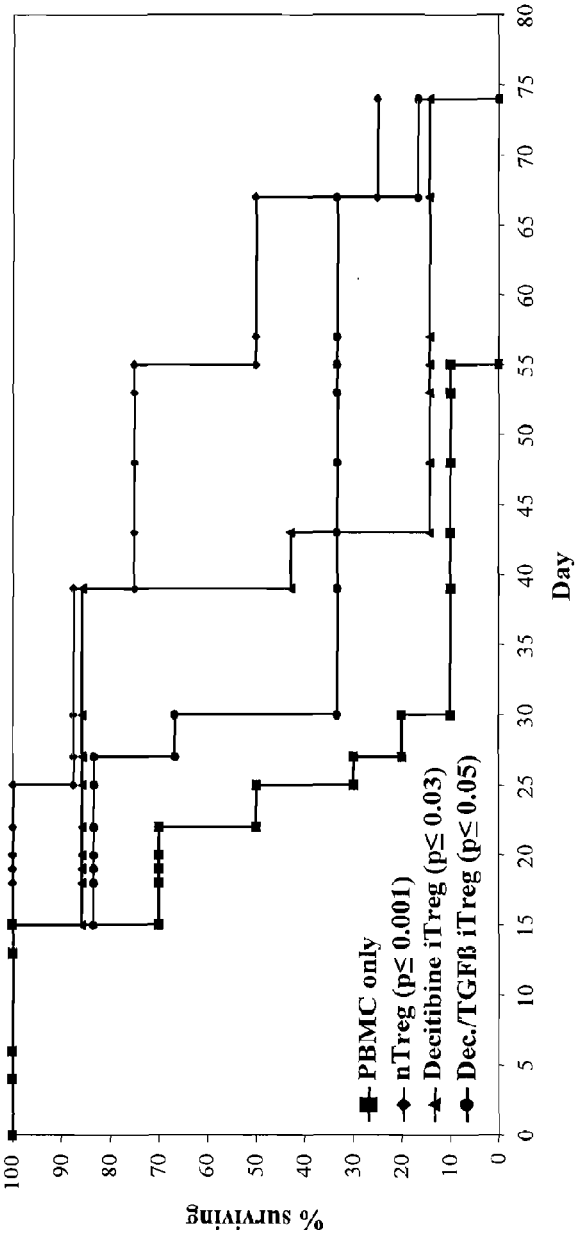

The next set of experiments were designed to evaluate the effects of Decitibine and Decitibine/TGFβ induced Tregs in a xenogeneic model of GVHD. Briefly, nTreg (CD4+25++) and CD4+25–45RA+ T cells were purified and expanded with cell based aAPC (KT64/86 at day 0 and 7) and cultured in the presence of Decitibine or Decitibine/TGFβ as discussed elsewhere herein. On day 14, nTreg, Decitibine iTreg, or Decitibine/TGFβ iTreg were co-transferred with allogeneic PBMC into clodronate-treated, irradiated Rag2$^{-/-}$, γ$_c$$^{-/-}$ mice. FIG. 9A depicts flow phenotype at Day 4 of the number of CD4+Foxp3+ per μl blood for each of the cell lines used. FIG. 9B represents a Kaplan-Meyer survival curve showing increased survival of clodronate-treated, irradiated Rag2$^{-/-}$, γ$_c$$^{-/-}$ mice receiving human PBMC±groups of Treg in a 3:1 ratio (i.e. 30- and 10×106 cells, respectively). n=10, 8, 7 and 6 for groups PBMC, nTreg, Decitibine iTreg and Decitibine/TGFβ iTreg respectively. P≤0.05 for each Treg treated group compared to PBMC.

The next set of experiments were designed to determine the feasibility of large-scale production of functionally suppressive, Foxp3+ induced Treg using Decitibine, or Decitibine plus TGFβ. Table 1 is a summary of the results from a representative large-scale purification and in vitro expansion experiment of Treg induced with Decitibine (n=3) or Decitibine plus TGFβ (n=4) in comparison to nTreg purified from umbilical cord (n=15) or peripheral blood (n=5). iTreg expansion was performed using a GMP-compliant cell line (KT64-86), and generated increased numbers of Foxp3+ cells (Total cell number * % CD4+25+Foxp3+) as compared to the clinical scale productions of umbilical cord or peripheral blood nTreg expanded with anti-CD3/28 beads (5- and 2-fold, respectively).

| | | Purification | | | | Expansion | | | |
| --- | --- | --- | --- | --- | --- | --- | --- | --- | --- |
| Source | Cell type | Initial cell number (×106) | Purified cell number (×106) | Initial % CD4+, 25++, FoxP3+ | Purified % CD4+, 25++, FoxP3+ | Expansion (Fold) | Final cell number* (×106) | % CD4, CD25+, Foxp3+ | Suppression index |
| UCB | nTreg | 2171 ± 258 | 7.5 ± 2.3 | 3.6 ± 1.4 | 45 ± 5 | 583 ± 127 | 6960 ± 2571 | 52 ± 8 | 1:2-1:64 (73% @ 1:4) |
| PB | nTreg | 12,800 (±1350) | 196 (±20) | 2.9 (±0.6) | 41 (±6) | 69 (±22) | 14,200 (±6160) | 62 (±7) | 1:4-1:64 (70% @ 1:4) |
| | Decitibine iTreg* | | 338 (±103) | N/A | N/A | 64.5 (±3.1) | 21801 (±1048) | 36.6 (±4) | 1:2-1:8 (48% @ 1:4) |
| | Decitibine/TGFβ iTreg* | | | | | 82.2 (±25.2) | 27784 (±12753) | 71 (±17) | 1:2-1:8 (62% @ 1:4) |

*Calculated total cell number from experiments initiated with 2 × 109 PBMC.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A method of generating and expanding an inducible T regulatory cell (iTreg), said method comprising
    isolating a non-Treg from peripheral blood, wherein said non-Treg is selected from the group consisting of a CD4$^+$cell, a CD4$^+$CD25$^-$cell, and a CD4$^+$CD25$^-$CD45RA$^+$cell;
    contacting the non-Treg with a combination of agents capable of converting said non-Treg into an iTreg, wherein the combination of agents comprise a tryptophan catabolite, and a demethylating agent selected from the group consisting of 5-aza-2'-deoxycitidine, 5-Azacytidine, and any combination thereof;
    contacting the iTreg with a mTOR inhibitor separate from the combination of agents, wherein the mTOR inhibitor inhibits non-Treg growth and is selected from the group consisting of tacrolimus, rapamycin, rapamycin derivative, and any combination thereof; and
    expanding the iTreg under appropriate growth conditions.

2. The method of claim 1, wherein said combination of agents further comprises an agent selected from the group consisting of a breakdown product of tryptophan, a histone deacetylase inhibitor (HDACi), and any combination thereof.

3. The method of claim 2, wherein said HDACi is selected from the group consisting of trichostatin A (TSA), suberoylanilide hydroxamic acid (SAHA), and any combination thereof.

4. The method of claim 1, wherein said iTreg is CD4$^+$CD25$^+$.

5. The method of claim 1, wherein said non-Treg is isolated from a sample obtained from leukopheresis products, bone marrow, lymph tissue, thymus tissue, spleen tissue, or umbilical cord tissue.

6. The method of claim 1, wherein said tryptophan catabolite is kynurenines.

7. The method of claim 1, wherein said mTOR inhibitor is rapamycin.

8. The method of claim 1, further comprising contacting said non-Treg with a bead or artificial antigen-presenting cell (aAPC) expansion system prior to or simultaneously with said combination of agents.

9. The method of claim 8, wherein the bead comprises an anti-CD3 antibody and an anti-CD28 antibody.

10. The method of claim 1, wherein said iTreg is positive for Foxp3.

11. The method of claim 1, further comprising contacting said iTreg with a bead or artificial antigen-presenting cell (aAPC) expansion system subsequent to contacting said non-Treg with said combination of agents.

12. The method of claim 11, wherein said aAPC comprises an anti-CD3 antibody and an anti-CD28 antibody.

13. The method of claim 1, wherein the iTreg is a human cell.

* * * * *